(12) United States Patent
Hirakawa

(10) Patent No.: US 8,211,010 B2
(45) Date of Patent: Jul. 3, 2012

(54) ENDOSCOPE INFORMATION PROCESSOR AND PROCESSING METHOD

(75) Inventor: Katsumi Hirakawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 1078 days.

(21) Appl. No.: 10/515,668

(22) PCT Filed: Oct. 29, 2003

(86) PCT No.: PCT/JP03/13829
§ 371 (c)(1),
(2), (4) Date: Nov. 23, 2004

(87) PCT Pub. No.: WO2004/039249
PCT Pub. Date: May 13, 2004

(65) Prior Publication Data
US 2005/0228221 A1 Oct. 13, 2005

(30) Foreign Application Priority Data

Oct. 29, 2002 (JP) .................................. 2002-314699
Jun. 6, 2003 (JP) .................................. 2003-162844

(51) Int. Cl.
*A61B 1/00* (2006.01)
*A61B 5/05* (2006.01)
(52) U.S. Cl. ................... 600/118; 600/117; 600/424
(58) Field of Classification Search ............... 600/101, 600/145, 424, 150, 103, 106, 114–118, 104, 600/146; 128/898
See application file for complete search history.

(56) References Cited

U.S. PATENT DOCUMENTS

| 5,060,632 | A | * | 10/1991 | Hibino et al. | 600/109 |
|---|---|---|---|---|---|
| 5,482,029 | A | * | 1/1996 | Sekiguchi et al. | 600/109 |
| 5,913,820 | A | * | 6/1999 | Bladen et al. | 600/407 |
| 5,997,473 | A | * | 12/1999 | Taniguchi et al. | 600/117 |
| 6,059,718 | A | * | 5/2000 | Taniguchi et al. | 600/117 |
| 6,175,756 | B1 | * | 1/2001 | Ferre et al. | 600/424 |
| 6,432,041 | B1 | * | 8/2002 | Taniguchi et al. | 600/118 |
| 6,511,417 | B1 | * | 1/2003 | Taniguchi et al. | 600/117 |
| 6,589,163 | B2 | * | 7/2003 | Aizawa et al. | 600/118 |
| 6,689,049 | B1 | * | 2/2004 | Miyagi et al. | 600/117 |
| 6,690,963 | B2 | * | 2/2004 | Ben-Haim et al. | 600/424 |
| 6,745,065 | B2 | * | 6/2004 | Niwa et al. | 600/424 |
| 6,773,394 | B2 | * | 8/2004 | Taniguchi et al. | 600/117 |
| 2002/0035321 | A1 | * | 3/2002 | Bucholz et al. | 600/407 |
| 2002/0156345 | A1 | * | 10/2002 | Eppler et al. | 600/114 |
| 2002/0183590 | A1 | * | 12/2002 | Ogawa | 600/117 |
| 2002/0183592 | A1 | * | 12/2002 | Suzuki et al. | 600/145 |
| 2003/0055317 | A1 | * | 3/2003 | Taniguchi et al. | 600/117 |
| 2010/0249507 | A1 | * | 9/2010 | Prisco et al. | 600/117 |

FOREIGN PATENT DOCUMENTS

JP 6-261858 9/1994
JP 08-010263 1/1996

(Continued)

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

An endoscopic information processing system in accordance with the present invention comprises: a shape analyzing unit that analyzes an insertional shape acquired by detecting the shape of an insertion unit of an endoscope which is inserted into a body cavity; and an information providing unit that provides information on the situation of handling the endoscope according to the result of the analysis performed by the shape analyzing unit.

25 Claims, 25 Drawing Sheets

FOREIGN PATENT DOCUMENTS

| JP | 8-107875 | 4/1996 |
| JP | 11-19027 | 1/1999 |
| JP | 2000-175861 | 6/2000 |
| JP | 2000-189379 | 7/2000 |
| JP | 2001-46332 | 2/2001 |
| JP | 2002-546 | 1/2002 |
| JP | 2002-345725 | 12/2002 |
| JP | 2003-144386 | 5/2003 |

* cited by examiner

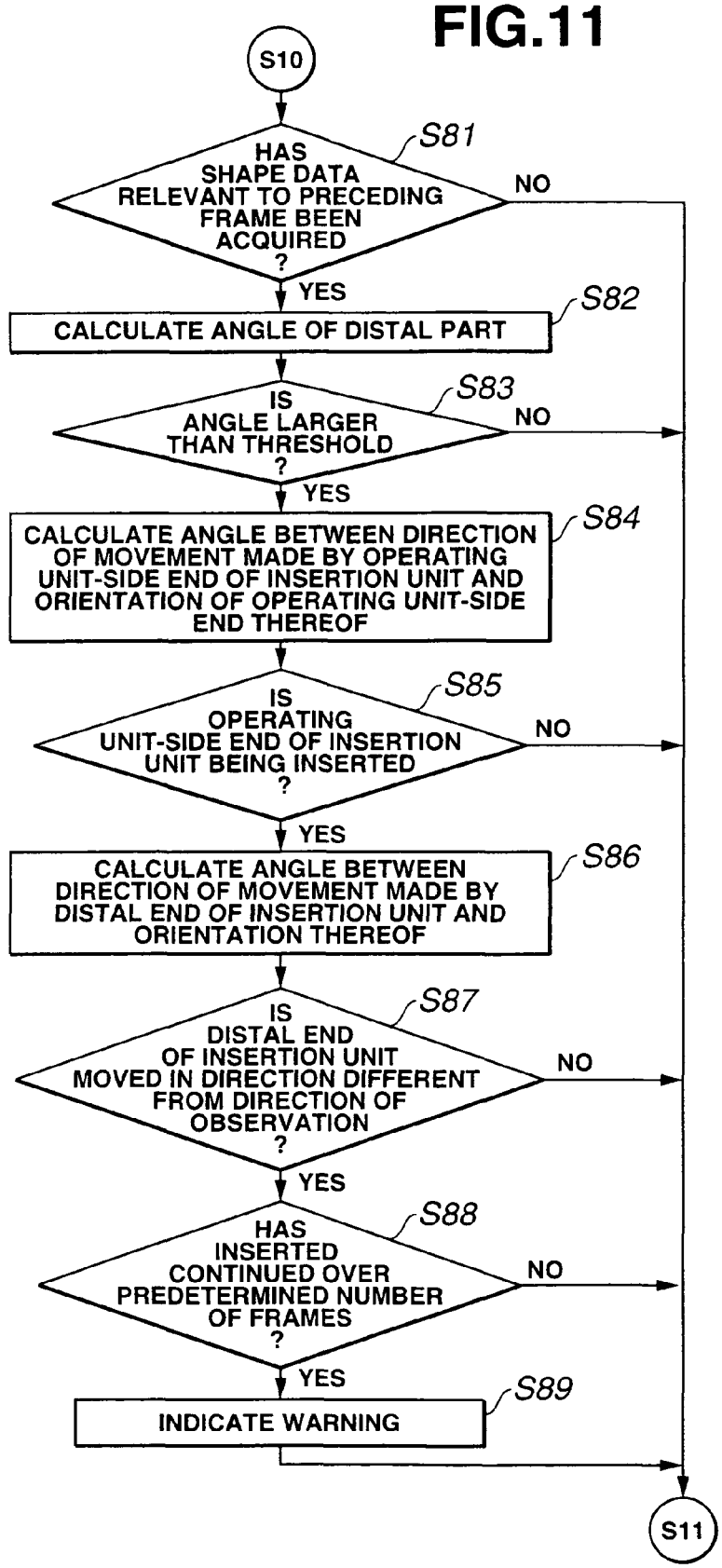

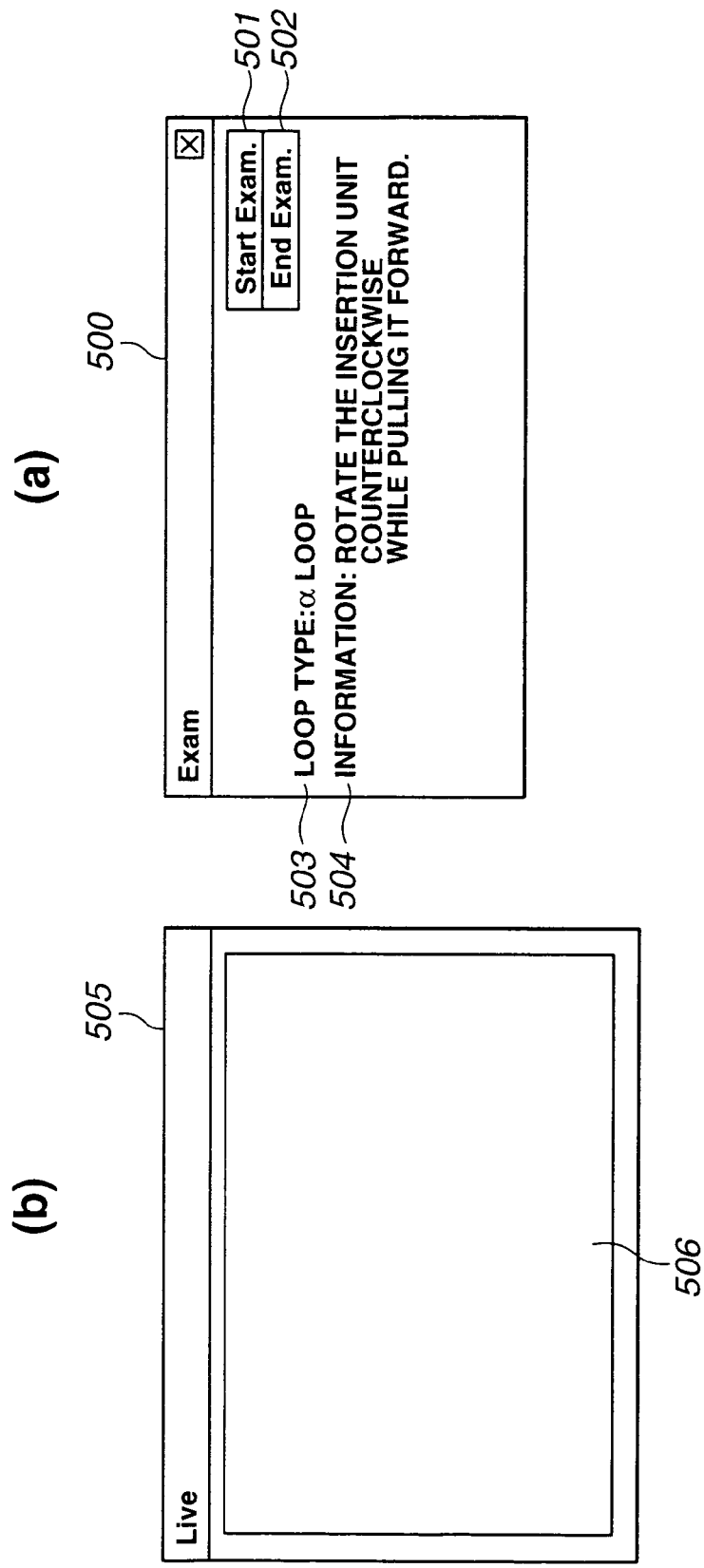

ENDOSCOPE INFORMATION PROCESSOR AND PROCESSING METHOD

TECHNICAL FIELD

The present invention relates to an insertional shape-of-endoscope analyzing system that analyzes the insertional shape of an endosdope insertion unit in a body cavity, displays an image according to the insertional shape information, and thus contributes to improvement in the insertional maneuverability of an endoscope.

BACKGROUND ART

In general, electronic endoscopes have an insertion unit that is elongated and flexible and that has an electronic image pickup device incorporated in the distal part thereof. The insertion unit is externally inserted into an object that is the lumen of a body cavity, and an image is reproduced on a monitor screen according to an image signal produced by the electronic image pickup device incorporated in the distal part of the insertion unit. The object is observed by viewing the reproduced image. Moreover, treatment forceps are passed through a forceps channel formed in the insertion unit, and used to collect a living tissue or to cure or treat the object.

By the way, the lumen of a body cavity is so tortuous as, for example, the large and small intestines are. When an endoscope is inserted into the tortuous lumen for observation, if it is discernible to what position in the lumen the endoscope insertion unit has been inserted or what is the shape of the endoscope insertion unit, the maneuverability of the endoscope for observation or treatment improves.

A proposal has been made of a shape-of-endoscope detecting system that can detect the position in a lumen, to which an endoscope insertion unit has been inserted, or the insertional shape of the insertion unit while being harmless to a human body that is an object, and that can be used for any lumen.

For example, according to a shape-of-endoscope detecting system (for example, Japanese Unexamined Patent Application Publication No. 8-107875 (from [0017] to [0178] and FIG. 1 to FIG. 13), a probe having a probe source coil incorporated therein is passed through a channel formed in an insertion unit of an endoscope. A magnetic field generation driving signal is applied to the probe source coil. A plurality of triaxial sense coils located at predetermined positions on a patient couch on which a subject lies down detect a magnetic field induced by the probe source coil. Based on signals detected by the sense coils, the position of the probe source coil is calculated. Shape image information concerning the insertion unit is produced in consideration of the calculated position. An image expressing the shape of the insertion unit is displayed on a monitor according to the shape image information. Images expressing shapes viewed in the directions of different viewing points that are orthogonal to each other are also produced. Two screen images can be simultaneously displayed on the monitor.

Moreover, according to another shape-of-endoscope detecting system (for example, Japanese Unexamined Patent Application Publication No. 2000-175861 (from [0011] to [0049] and FIG. 1 to FIG. 10), a source coil comprises a plurality of first coils, and a sense coil comprises a plurality of second coils that detects a magnetic field induced by the plurality of first coils constituting the source coil. One of the source coil and the sense coil is disposed in an insertion unit of an endoscope that is inserted into a body cavity. A shape inferring means infers the shape of the endoscope insertion unit from the magnetic field induced by the source coil and detected by the sense coil. Herein, it is detected whether the shape of the insertion unit inferred by the shape inferring means is a specific shape. If the specific shape is detected, a warning is given.

Conventionally, while an object is being examined using an endoscope, the operator's conscious is concentrated on an endoscopic image expressing a region to be observed in a lumen. A shape-of-insertion unit image produced by a shape-of-endoscope insertion unit detecting system is viewed only when it is needed. This is a typical style of endoscopic examination.

The Japanese Unexamined Patent Application Publication No. 8-107875 has proposed a shape-of-endoscope detecting system having an endoscope insertion supporting capability. Namely, during the endoscopic examination, if the insertion unit is looped, the looping is detected and a warming is given in order to alert an operator.

Furthermore, there is a demand for provision of information according to the movement of an endoscope insertion unit that is actually inserted or provision of information on a way of inserting an endoscope or information on a directive concerning handling. This would contribute to improvement in ease of insertion.

The present invention attempts to meet the foregoing demand. An object of the present invention is to provide a shape-of-endoscope insertion unit analyzing system capable of analyzing the shape of an endoscope insertion unit and providing information that contributes to improvement in the ease of insertion of an endoscope.

Conventionally, while an operator is observing an object using an endoscope, the operator's conscious is concentrated on an endoscopic image produced to express a region to be observed, mainly, in a lumen. The operator is often unconscious of a shape-of-insertion unit image produced and displayed by a shape-of-endoscope insertion unit detecting system. The operator does not pay attention to the image expressing the shape of the insertion unit until the progress in inserting the endoscope insertion unit is hindered. This becomes a factor of hindering the progress in endoscopic observation or causing patient discomfort.

In efforts to speed up the progress in endoscopic observation or eliminate patient discomfort, the shape-of-endoscope detecting system disclosed in the Japanese Unexamined Patent Application Publication No. 8-107875 is designed to simultaneously display on a monitor screen an endoscopic image expressing a region to be observed and a shape-of-insertion unit image. Therefore, since the operator's conscious is directed to both the images, the progress in endoscopic observation can be facilitated and patient discomfort can be eliminated.

Moreover, a shape-of-endoscope detecting system disclosed in Japanese Unexamined Patent Application Publication No. 2000-175861 is intended not to cause patient discomfort. Namely, when an endoscope insertion unit is looped while being inserted into a lumen, it causes patient discomfort. Therefore, when the insertion unit is likely to loop in a lumen, the looped shape is detected and a warning is given in order to alert an operator.

In relation to the foregoing shape-of-endoscope detecting systems, no suggestion is made for recording an endoscopic image of an object and a shape-of-insertion unit image. In general, an endoscopic image is recorded during endoscopic observation and used to confirm an observed region later or employed in the training for getting the knack of handling an endoscope.

For recording of an endoscopic image and a shape-of-insertion unit image, video equipment is usually adopted.

Since the endoscopic image and the shape-of-insertion unit image are recorded in different pieces of video equipment, when the images are reproduced, they may become inconsistent with each other. For simultaneously recording of both the endoscopic image and shape-of-insertion unit image in sole video equipment, special video equipment is needed.

Japanese Patent Application No. 2001-347909 has proposed an endoscopic image filing system in which both an image expressing the shape of an insertion unit detected by a shape-of-endoscope detecting system and an endoscopic image are recorded. More particularly, the endoscopic image is recorded in association with the shape-of-insertion unit image.

However, in the endoscopic image filing system proposed in the Japanese Patent Application No. 2001-347909, an endoscopic image and a shape-of-insertion unit image produced when a Release button on an endoscope is handled are recorded in the form of still images. The recorded images are therefore unsuitable for use in checking the entire process of endoscopic observation from the beginning to the end or in the training for handling an endoscope.

Moreover, no suggestion has been made for the capability to append information to any frame of an endoscopic image or of a shape-of-insertion unit image or to display the appended information during synchronous reproduction of the images. There is a demand for an endoscopic image processing system that can record or preserve the endoscopic image and shape-of-insertion unit image that express an object and the shape of an insertion unit throughout endoscopic examination, and that enables entry of supplementary information to be appended to the recorded or preserved image.

In consideration of the above demand, an object of the present invention is to provide an endoscopic image processing system capable of preserving both data representing the insertional shape of an endoscope and data representing an endoscopic image, and capable of synchronously reproducing both the images.

Another object of the present invention is to provide an endoscopic image processing system capable of appending relevant information to endoscopic image data or insertional shape data, and capable of presenting the relevant information during synchronous reproduction of the preserved insertional shape data and endoscopic image data.

DISCLOSURE OF INVENTION

An endoscopic information processing system in accordance with the present invention comprises: a shape analyzing unit that analyzes an insertional shape acquired by detecting the shape of an insertion unit of an endoscope that is inserted into a body cavity and; and an information providing unit that provides information on the situation of handling an endoscope according to the result of the analysis performed by the form analyzing unit.

BRIEF DESCRIPTION OF THE DRAWINGS

FIG. 11 is a flowchart describing an operation detecting the angle of a distal endoscope section and giving a warning that is provided by an electronic endoscopic system employing a fourth embodiment of the present invention;

FIG. 29 shows display screen images displayed during search for a feature of an endoscopic image or an insertional shape-of-endoscope image that is executed in the electronic endoscopic system employing the eighth embodiment of the present invention.

BEST MODE FOR CARRYING OUT THE INVENTION

Figure 1:
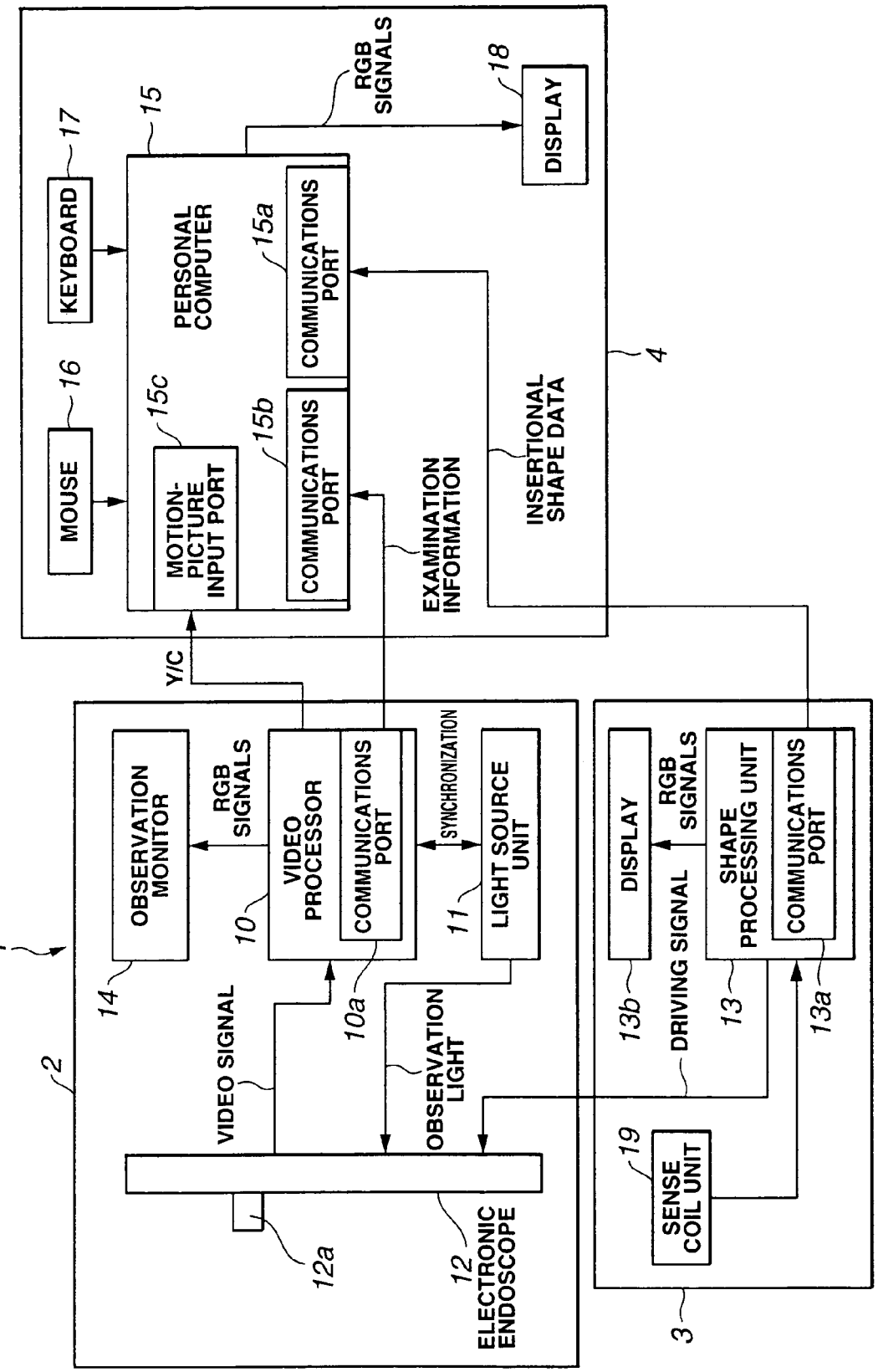
FIG. 1 is a block diagram showing the overall configuration of an electronic endoscopic system employing a first embodiment of the present invention.

Referring to the drawings, embodiments of the present invention will be described below.

To begin with, a first embodiment of the present invention will be described in conjunction with FIG. 1 to FIG. 6.

Figure 2:
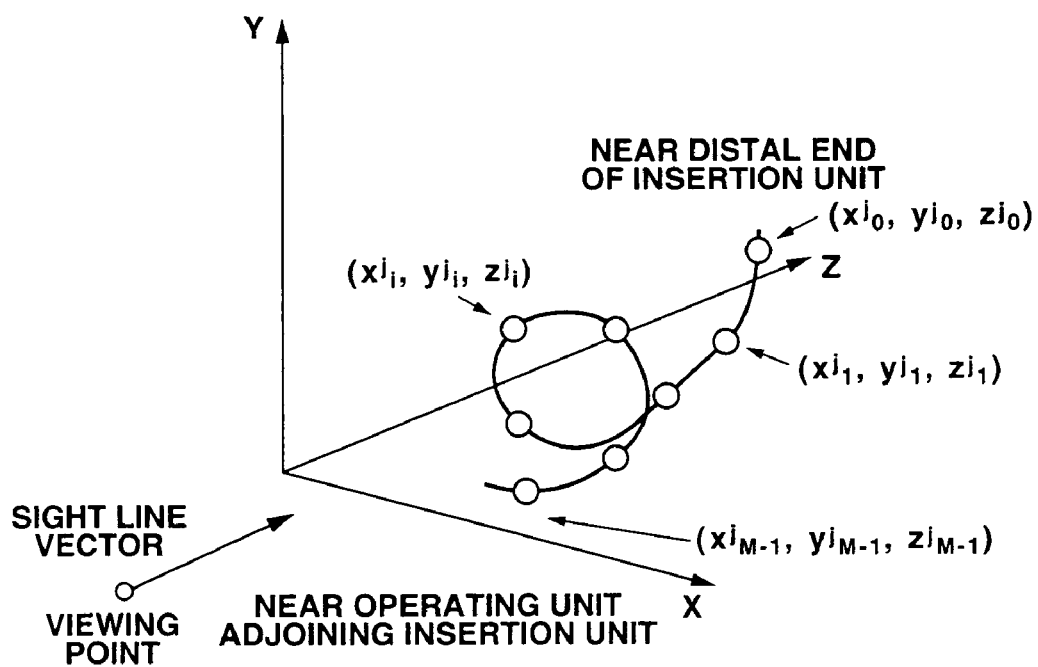
FIG. 2 is an explanatory diagram showing a coordinate system defined to represent a position to which an insertion unit included in the electronic endoscopic system employing the first embodiment is inserted.
Figure 3:
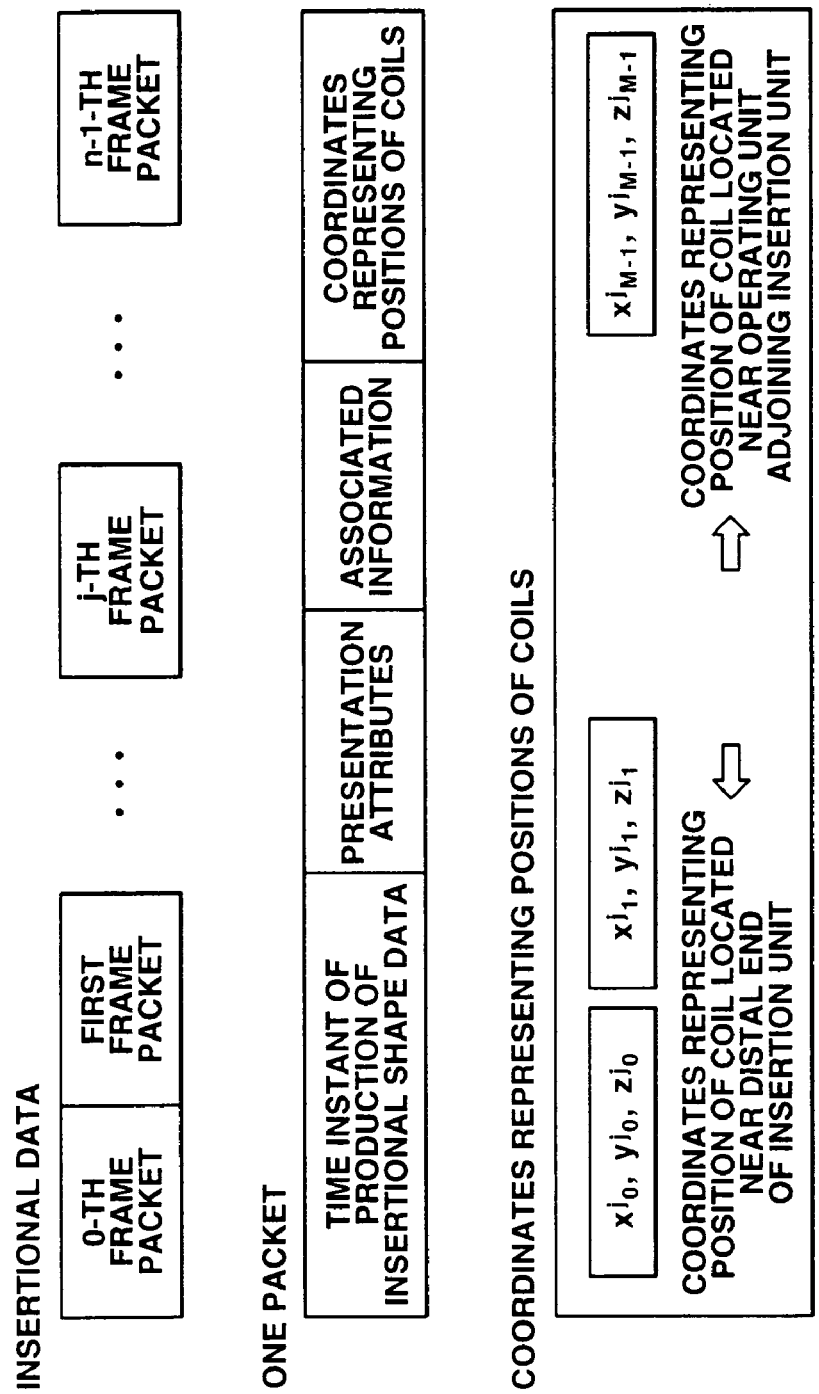
FIG. 3 is an explanatory diagram showing the data structure of inserted position detection data produced by an insertional shape-of-endoscope observing system included in the electronic endoscopic system employing the first embodiment.
Figure 4:
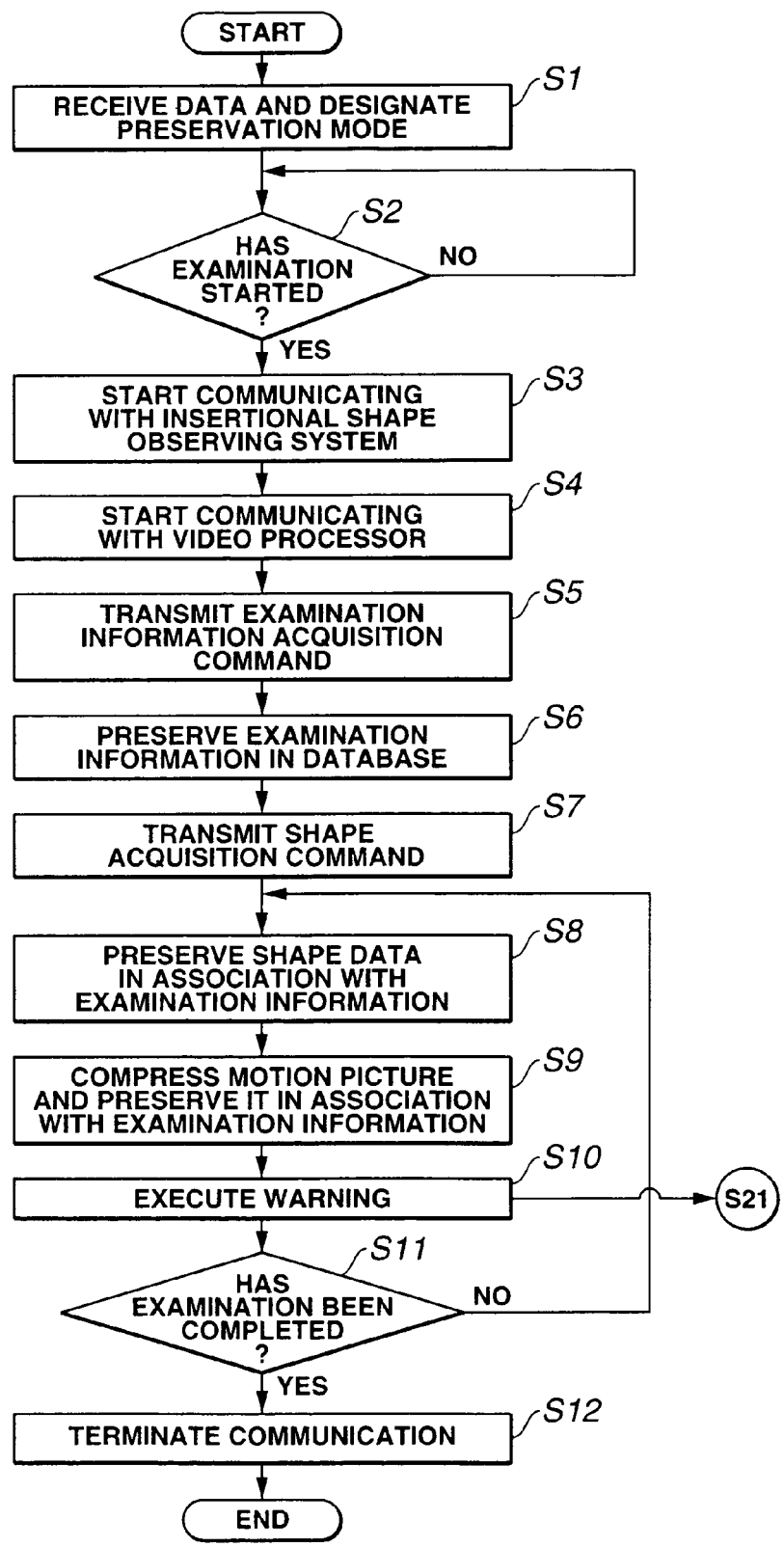
FIG. 4 is a flowchart describing a process to be executed in the electronic endoscopic system employing the first embodiment.
Figure 5:
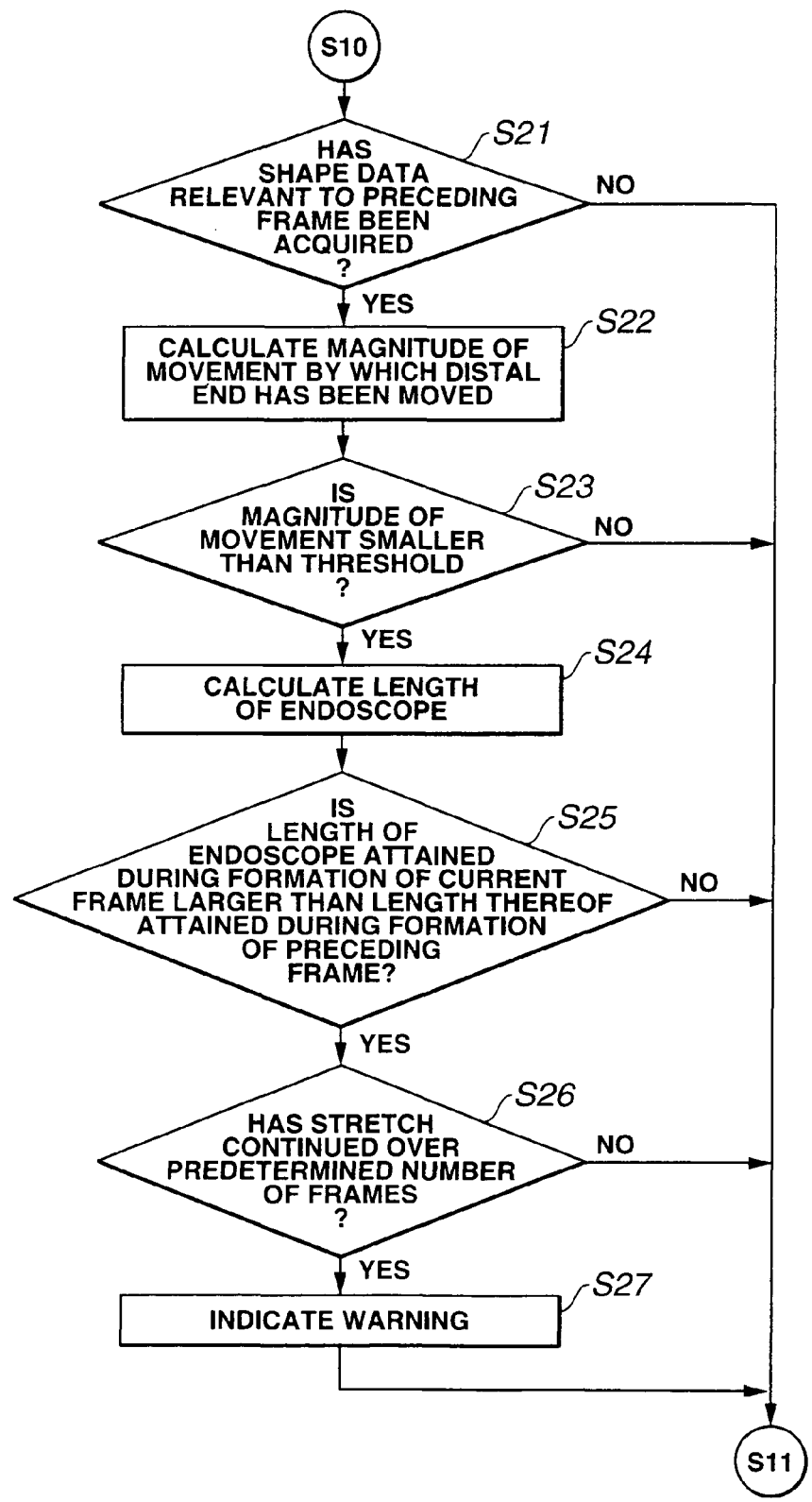
FIG. 5 is a flowchart describing an operation of detecting a stretch made by an object which is provided by the electronic endoscopic system employing the first embodiment.
Figure 6:
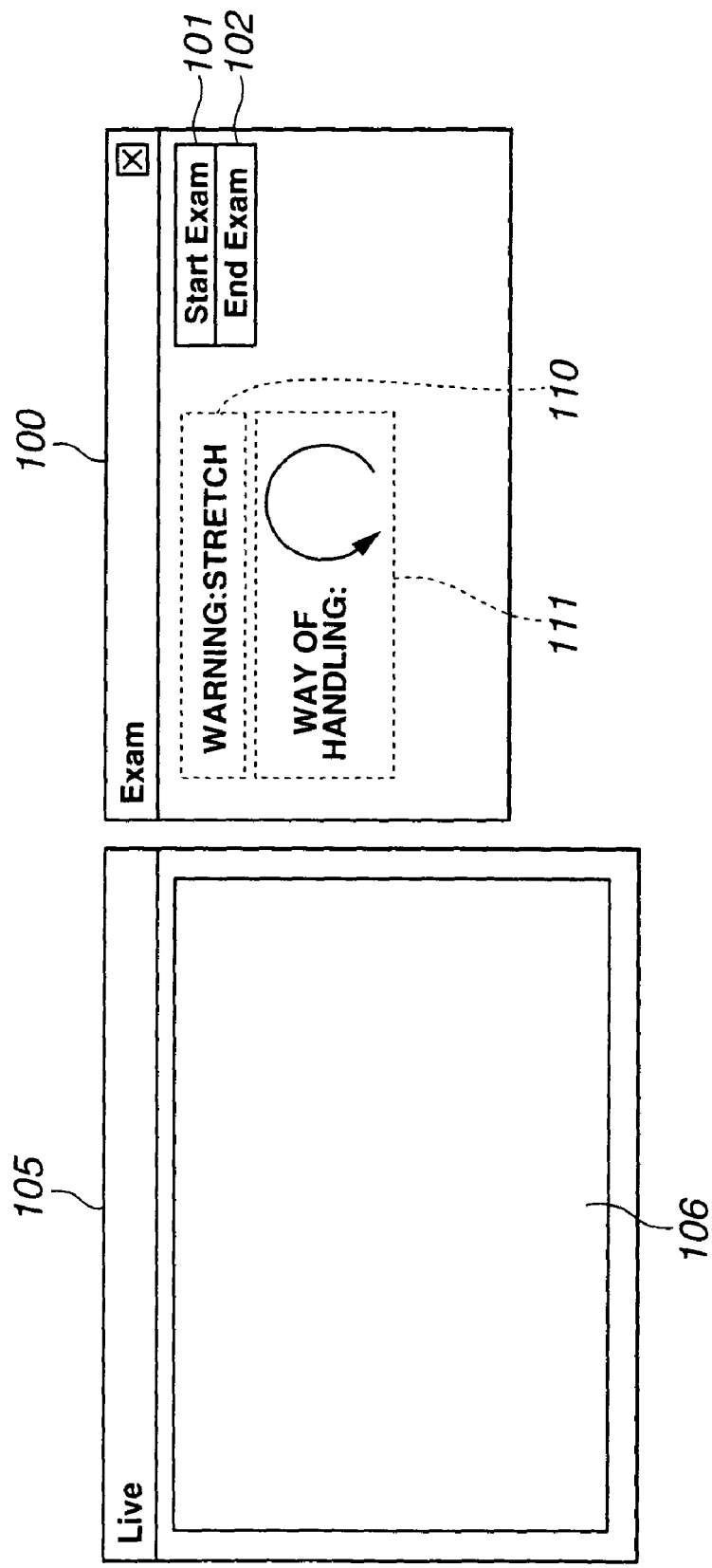
FIG. 6 is an explanatory diagram showing a display screen image displayed on a display during endoscopic examination performed using the electronic endoscopic system employing the first embodiment.

FIG. 1 is a block diagram showing the overall configuration of an electronic endoscopic system employing the first embodiment of the present invention. FIG. 2 is an explanatory diagram showing a coordinate system representing an inserted position to which an insertion unit included in the electronic endoscopic system employing the first embodiment is inserted. FIG. 3 is an explanatory diagram showing the data structure of inserted position detection data produced by an insertional shape-of-endoscope observing system included in the electronic endoscopic system employing the first embodiment. FIG. 4 is a flowchart describing a process to be executed in the electronic endoscopic system employing the first embodiment. FIG. 5 is a flowchart describing an operation of detecting a stretch made by an object that is provided by the electronic endoscopic system employing the first embodiment. FIG. 6 is an explanatory diagram showing display screen images that are displayed on a display during endoscopic examination performed using the electronic endoscopic system employing the first embodiment.

Referring to FIG. 1, a description will be made of the electronic endoscopic system 1 employing an image processing system in accordance with the first embodiment of the present invention that analyzes the insertional shape of an endoscope.

The electronic endoscopic system 1 comprises an endoscope system 2, an insertional shape-of-endoscope observing system 3, and an image processing system 4.

The endoscope system 2 comprises an electronic endoscope 12, a video processor 10, a light source unit 11, and an observation monitor 14.

The electronic endoscope 12 has an electronic image pickup device incorporated in the distal part of an elongated insertion unit thereof that is inserted into the lumen of a body cavity that is an object, though the electronic image pickup device is not shown. The electronic image pickup device is driven or controlled in order to produce and transmit an image pickup video signal representing a region to be observed in the lumen. Observation light with which the region to be observed in the lumen is illuminated is irradiated by a light guide lying through the insertion unit.

Furthermore, the distal part of the insertion unit of the electronic endoscope 12 includes a bending section that can be bent using an operating unit formed at the proximal end of the insertion unit.

Furthermore, the operating unit of the electronic endoscope 12 has a Release switch 12a. A cable over which the electronic image pickup device is driven or controlled or a produced image video signal is transmitted or received to or from the video processor 10 is extended from the operating unit. A light guide cable over which observation light emanating from the light source unit 11 is introduced to the light guide is extended from the operating unit.

Moreover, the electronic endoscope 12 includes a detecting facility that detects the inserted position or form of the insertion unit in a lumen, though the detecting facility is not shown. The detecting facility that detects the inserted position or insertional shape of the insertion unit comprises a plurality of source coils that is disposed in the insertion unit of the endoscope with a predetermined space between adjoining source coils, and a sense coil unit 19 having a plurality of sense coils disposed in the insertional shape-of-endoscope observing system 3.

The video processor 10 drives or controls the electronic image pickup device incorporated in the electronic endoscope 12. Moreover, the video processor 10 performs predetermined signal processing on a motion-picture video signal resulting from photoelectric conversion performed by the electronic image pickup device so as to produce a luminance signal and a color signal (Y/C signals) or red, green, and blue signals (RGB signals).

The luminance and Y/C signals or the RGB signals produced by the video processor 10 are transmitted directly to the observation monitor 14 and image processing system 15.

Moreover, when the Release switch 12a is handled, display of a still image of a picked-up image can be directed.

The video processor 10 has a facility for receiving examination information on endoscopic examination, though the facility is not shown.

The light source unit 11 comprises a lamp that is an illumination light source and a circuit for lighting the lamp. Illumination light radiated with the lamp lit is fed to the light guide lying through the electronic endoscope 12, and irradiated to a region to be observed in a lumen through the distal end of the insertion unit.

On the observation monitor 14, an endoscopic image is displayed based on the Y/C signals or RGB signals produced by the video processor 10.

The insertional shape-of-endoscope observing system 3 is a peripheral device of the endoscope system 2. The insertional shape-of-endoscope observing system 3 comprises: a sense coil unit 19 that detects a magnetic field induced by the source coils incorporated in the electronic endoscope 12; a shape processing unit 13 that infers the shape of the endoscope insertion unit on the basis of the magnetic field detected by the sense coil unit 19; and a monitor (display) 13b on which the shape of the endoscope insertion unit inferred by the shape processing unit 13 is presented.

The shape processing unit 13 transmits a driving signal, with which the source coils are driven, to the electronic endoscope 12 so that the source coils will induce a magnetic field. Based on a detection signal sent from the sense coil unit 19 that detects the magnetic field, data items representing the coordinates of the positions of the source coils are calculated. The shape of the endoscope insertion unit is inferred from the calculated data items representing the coordinates of the positions. Moreover, the shape processing unit 13 produces a shape-of-insertion unit image signal based on which the inferred shape of the endoscope insertion unit is presented through the monitor 13b. Furthermore, the shape processing unit 13 produces information on coordinates in the three-dimensional space that represents the shape of the endoscope insertion unit, and data representing an insertional shape and including attributes for presentation of the shape. The three-dimensional coordinate information and insertional shape data are transmitted to the image processing system 4.

Incidentally, the insertional shape-of-endoscope observing system 3 can modify the shape presentation attributes in response to the entry of a directive made at an operator panel that is not shown. The shape presentation attributes include an angle of rotation by which a shape-of-insertion unit image produced by the shape processing unit 13 and displayed on the monitor 13b is rotated, and an enlargement or reduction ratio for the shape-of-insertion unit image.

Insertional shape data produced by the shape processing unit 13 can be transmitted to the image processing system 4.

Incidentally, the insertional shape-of-endoscope observing system 3 continuously transmits insertional shape data to the image processing system 4 during endoscopic examination. Moreover, the insertional shape-of-endoscope observing system 3 can transmit only the insertional shape data that is acquired when the Release switch 12a included in the electronic endoscope 12 is handled.

The image processing system 4 includes a personal computer (PC) 15, a mouse 16 and a keyboard 17 for use in entering various directives that are transmitted to the PC 15, and a display 18 on which various kinds of data items or various pieces of image information that are treated by the PC 15 are reproduced and presented.

Furthermore, the PC 15 has: a communications port 15a through which insertional shape data sent through a communications port 13a of the shape processing unit 13 included in the insertional shape-of-endoscope observing system 3 is received; a communications port 15b through which endoscopic examination information sent through a communications port 10a of the video processor 10 included in the endoscope system 2 is received; and a motion picture input port 15c through which a motion picture video signal produced by the video processor 10 included in the endoscope 2 is converted into predetermined compressed image data.

In short, a video signal representing a motion picture and being produced by the video processor 10 is applied to the motion picture input port 15c of the image processing system 4. The motion-picture video signal is converted into predetermined compressed motion-picture video signal data, for example, compressed image data conformable to the MJPEG standard, and preserved in a recording device, which is not shown, included in the PC 15.

In general, before endoscopic examination is started, examination information on endoscopic examination is received from the video processor 10. Based on the received examination information, characters or numerals are displayed on the observation monitor 14. The examination information may be transmitted to the image processing system 4 through the communications ports 10a and 15b, and recorded therein.

What is referred to as examination information includes, for example, a patient name, a date of birth, a sex, an age, a patient code, and a date of examination and so on.

Namely, the image processing system 4 is connected to the video processor 10, if necessary, in order to receive and preserve various pieces of information from the video processor 10.

Production of insertional shape data in the insertional shape-of-endoscope observing system 3 included in the electronic endoscopic system 1 having the foregoing components will be described in conjunction with FIG. 2 and FIG. 3.

The insertional shape-of-endoscope observing system 3 produces insertional-shape data including coordinates in the three-dimensional space, which represent the positions of M source coils incorporated in the insertion unit of the electronic endoscope 12, for each frame represented by an image video signal produced by the electronic image pickup device incorporated in the electronic endoscope 12. Based on the insertional shape data, a shape-of-insertion unit image is produced and displayed on the display 13b. The insertional shape data is transmitted to the image processing system 4.

As shown in FIG. 2 a coordinate system by which coordinates are associated with the positions of the source coils detected by the insertional shape-of-endoscope observing system 3 specifies coordinates ($X^j_i$, $Y^j_i$, $Z^j_i$) in the three-dimensional space that represent the position of the i-th (where i denotes 0, 1, etc., or M−1) source coil detected during formation of the j-th frame. Noted that the source coils are orderly counted from the source coil located near the distal end of the insertion unit.

The insertional shape data containing the coordinates representing the positions of the source coils detected by the insertional shape-of-endoscope observing system 3 has the structure shown in FIG. 3. Data relevant to one frame is transmitted as one packet. One packet specifies a time instant at which insertional shape data is acquired or produced, presentation attributes, associated information, and the coordinates representing the positions of the source coils. As for the coordinates representing the positions of the source coils, the coordinates in the three-dimensional space representing the positions of the source coils incorporated in the insertion unit of the electronic endoscope 12 are juxtaposed in the order from the coordinates representing the position of the source coil located near the distal end of the insertion unit to the coordinates representing the position of the source coil located near the operating unit formed at the proximal end of the insertion unit. Incidentally, the coordinates representing the positions of source coils located outside a range of detection within which the insertional shape-of-endoscope observing system 3 can detect the positions of source coils are replaced with predetermined constants.

Next, a process of acquiring examination information and an endoscopic image from the video processor 10 included in the endoscope system 2 and insertional shape data from the shape processing unit 13 included in the insertional shape-of-endoscope observing system 3, and recording them, and detection of a stretch made by the large intestine that is an object will be described in conjunction with FIG. 4 to FIG. 6. The image processing system 4 executes the process and the detection.

The process is implemented by developing or running an examination application in the PC 15 included in the image processing system 4.

Before endoscopic examination is started, the video processor 10 receives examination information, and the PC 15 included in the image processing system 4 invokes the examination application. When the examination application is invoked, an examination window 100 and an endoscopic image window 105 shown in FIG. 6 are opened on the display 18.

When the examination application is developed or run in the PC 15 included in the image processing system 4, the examination window 100 is opened on the display 18. Consequently, at step S1, the PC 15 enters a mode in which the PC 15 receives examination information and endoscopic image data from the video processor 10 and insertional shape data from the shape processing unit 13 included in the insertional shape-of-endoscope observing system 3, and preserves them.

Thereafter, at step S2, the PC 15 judges whether an operator has turned on an examination start button (Start Exam. button) 101 displayed in the examination window 100 using the mouse 16 or keyboard 17. The PC 15 stands by until the examination start button 101 is turned on. When the examination start button is turned on, processing started at step S3 is executed.

At step S3, the PC 15 starts communicating with the shape processing unit 13 included in the insertional shape-of-endoscope observing system 3 through the communications port 15a. At step S4, the PC 15 starts communicating with the video processor 10 through the communications port 15b.

At step S5, the PC 15 transmits an examination information acquisition command to the video processor 10 through the communications port 15b and the communications port 10a of the video processor 10. In response to the examination information acquisition command, the video processor 10 transmits examination information to the PC 15.

At step S6, the PC 15 records or preserves the examination information, which is sent from the video processor 10 at step S5, in a recording device that is not shown.

Thereafter, at step S7, the PC 15 transmits an insertional shape data acquisition command to the shape processing unit 13 through the communications port 15a and the communications port 13a of the shape processing unit 13. In response to the insertional shape data acquisition command, the shape processing unit 13 starts transmitting insertional shape data. The transmission continues until communication between the PC 15 and the shape processing unit 13 is terminated and the communications port 15a is broken.

At step S8, the PC 15 receives insertional shape data that is sent from the shape processing unit 13 at step S7. The PC 15 records or preserves the insertional shape data in a file in a hard disk, which is not shown but included in the PC 15, in association with the examination information recorded or preserved at step S6 (hereinafter, the insertional shape data may be called a inserted-form file).

Thereafter, at step S9, the PC 15 converts a motion picture video signal, which is received from the video processor 10 through the motion picture input port 15c, into compressed image data conformable to the MJPEG standard. The PC 15 then records or preserves the compressed image data in a file in the hard disk of the PC 15, which is not shown, in association with the examination information recorded or preserved at step S6 (hereinafter, the compressed image data may be referred to as an image file). A motion picture received through the motion picture input port 15c is then displayed in an endoscopic image field 106 of the endoscopic image window 105 shown in FIG. 6.

Thereafter, at step S10, the PC 15 executes warning that starts at step S21 in FIG. 5. When the warning is terminated, the PC 15 judges at step S11 whether an examination end button (End Exam. button in the drawing) 102 included in the examination window 100 has been clicked. If it is judged that the examination end button 102 is not clicked, control is returned to step S8. If it is judged that the examination end button 102 has been clicked, the communications ports 15a and 15b are broken in order to terminate communication of information or data between the shape processing unit 13 and video processor 10.

The warning executed at step S10 will be described in conjunction with FIG. 5. The warning of step S10 is a process of detecting a stretch made by the large intestine that is an object. If the inserted length by which the endoscope insertion unit is inserted into the large intestine is increased with the distal end of the insertion unit of the electronic endoscope 12 nearly at a halt, the large intestine is thought to have stretched. Therefore, the inserted length of the endoscope insertion unit is measured in order to detect the stretch of the large intestine.

At step S21, the PC 15 judges whether insertional shape data relevant to a frame preceding a current frame relevant to insertional shape data is acquired and recorded at step S8 has already been acquired. If the insertional shape data relevant to the preceding frame has not been acquired, control is passed to processing started at step S11.

If it is judged at step S21 that the insertional shape data relevant to the preceding frame has been acquired, the PC 15 calculates at step S22 a magnitude of movement dif made by the distal end of the insertion unit of the electronic endoscope 12 using the insertional shape data items relevant to the preceding and current frames according to the following expression (1):

$$dif = |X_0^j - X_0^{j-1}| + |X_1^j - X_1^{j-1}| + \ldots + |X_{m-1}^j - X_{m-1}^{j-1}| + \quad \text{[expression 1]}$$
$$|Y_0^j - Y_0^{j-1}| + |Y_1^j - Y_1^{j-1}| + \ldots + |Y_{m-1}^j - Y_{m-1}^{j-1}| +$$
$$|Z_0^j - Z_0^{j-1}| + |Z_1^j - Z_1^{j-1}| + \ldots + |Z_{m-1}^j - Z_{m-1}^{j-1}|$$

The magnitude of movement dif provided by the expression (1) is calculated using m data items that represent the positions of m source coils started with the source coil located near the distal end of the insertion unit. The calculation of the magnitude of movement dif is not limited to the one based on the expression (1). Alternatively, an euclidean distance, that is, a distance defined in the three-dimensional euclidean space may be adopted.

A distance by which the distal end of the insertion unit has moved, that is, the magnitude of movement dif calculated using the expression (1) at step S22 is compared with a predetermined threshold at step S23. If the distance by which the distal end has moved, that is, the magnitude of movement dif is larger than the predetermined threshold, it is verified that the distal end of the insertion unit is being inserted. Control is then passed to the processing started at step S11. If the magnitude of movement dif is smaller than the threshold, it is verified that the distal end of the insertion unit is at a halt. The processing started at step S24 is executed.

At step S24, the PC 15 measures the length of the insertion unit of the electronic endoscope 12 that is sensed by the shape processing unit 13 included in the insertional shape-of-endoscope observing system 3 during formation of the current frame. The length of the insertion unit of the electronic endoscope 12 is calculated based on, for example, the number of effective sets of coordinates representing the positions of source coils among all the sets of coordinates specified in the insertional shape data produced by the shape processing unit 13.

Thereafter, at step S25, the PC 15 compares the length of the insertion unit attained during formation of the current frame, which is calculated at step S24, with the length of the endoscope insertion unit attained during formation of a frame preceding the current frame. If the result of the comparison performed at step S25 demonstrates that the length of the endoscope insertion unit attained during formation of the current frame is larger than the length thereof attained during formation of the preceding frame, it is verified that the insertion unit is being inserted. Control is then passed to processing started at step S11. If the length of the endoscope insertion unit attained during formation of the current frame is smaller than the length thereof attained during formation of the preceding frame, it is verified that the insertion unit is at a halt or being pulled. Processing started at step S26 is executed.

At step S25, if the length of the insertion unit attained during formation of the current frame is smaller than the length thereof attained during formation of the preceding frame, the PC 15 verifies that the large intestine has not yet stretched. At step S26, the PC 15 verifies whether the distal end of the insertion unit of the endoscope comes to a halt and whether the length of the endoscope insertion unit attained during formation of a current frame is larger than the length thereof attained during formation of a preceding frame over a predetermined number of frames.

Assume that it is verified at step S26 that the distal end of the insertion unit of the electronic endoscope is at a halt but that the increase in the length of the insertion unit attained during formation of a preceding frame has not continued over the predetermined number of frames. In this case, it is verified that the large intestine has not stretched. Processing started at step S11 is then executed. If the distal end of the insertion unit of the electronic endoscope is at a halt and the increase in the length of the insertion unit continues over the predetermined number of frames, it is verified that the large intestine has stretched. Consequently, step S27 is executed.

At step S27, the PC 15 produces a warning signal with which an operator is alerted to the stretch of the large intestine. The PC 15 then generates a warning sound so as to provide information on the shape of the endoscope insertion unit or displays a warning message in a warning indicator section 110 of the examination window 100 shown in FIG. 6. The warning indication is not limited to characters. Alternatively, an icon or any other graphical indication may be displayed in a warning graphic indicator section 111, or a warning indication may be flickered.

As mentioned above, the image processing system in accordance with the present invention uses a plurality of insertional shape data items relevant to a current frame and a preceding frame to provide information on the shape of the endoscope insertion unit according to the movement of the actually inserted endoscope insertion unit. The image processing system readily and quickly detects or verifies the stretch of the large intestine that is a region to be observed, and immediately warns an operator.

Incidentally, the image processing system 4 has been described in terms of the ability to detect the stretch of the large intestine on the basis of the insertional shape data received from the insertional shape observing system 3 so as to give a warning. If a viewer that enables browsing of endoscopic image data and insertional shape data is made available, the stretch of the large intestine may be detected relative to designated insertional shape data.

Figure 7:
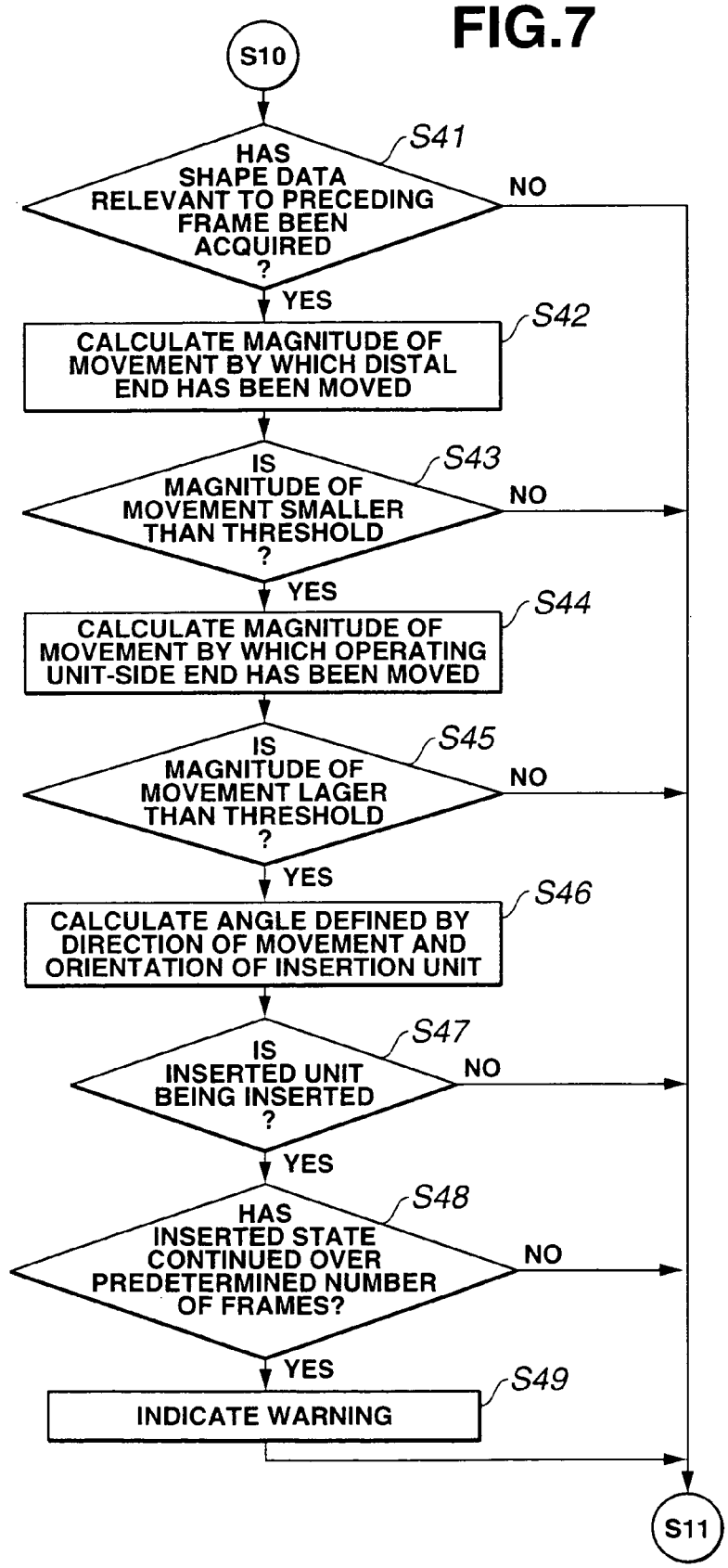
FIG. 7 is a flowchart describing an operation of detecting the angle of a distal endoscope section included in an electronic endoscopic system employing a second embodiment.

Next, a second embodiment of the present invention will be described in conjunction with FIG. 7 and FIG. 8.

The configuration of the electronic endoscopic system 1 employing the second embodiment is identical to that of the electronic endoscopic system employing the first embodiment. The image processing system 4 treats endoscopic image data received from the endoscope system 2 and insertional shape data received from the insertional shape-of-endoscope observing system 3 in fundamentally the same manner as the image processing system in accordance with the first embodiment.

A difference of the second embodiment from the first embodiment lies in the warning executed at step S10 in the image processing system 4. The warning executed at step S10 in the second embodiment comprises steps started with step S41 and described in FIG. 7.

At step S41, the PC 15 verifies whether insertional shape data relevant to a frame preceding the current frame that has relevant insertional shape data acquired and preserved at step S8 has been acquired. If the insertional shape data relevant to the preceding frame has not been acquired, control is passed to processing started at step S11.

If it is verified at step S41 that the insertional shape data relevant to the preceding frame has been acquired, the PC 15 uses the insertional shape data items relevant to the preceding and current frames to calculate a magnitude of movement dif1, by which the distal end of the insertion unit of the electronic endoscope 12 has moved, according to the following expression (2).

$$dif1 = |X_0^j - X_0^{j-1}| + |X_1^j - X_1^{j-1}| + \ldots + |X_{m1-1}^j - X_{m1-1}^{j-1}| + \quad \text{[expression 2]}$$
$$|Y_0^j - Y_0^{j-1}| + |Y_1^j - Y_1^{j-1}| + \ldots + |Y_{m1-1}^j - Y_{m1-1}^{j-1}| +$$
$$|Z_0^j - Z_0^{j-1}| + |Z_1^j - Z_1^{j-1}| + \ldots + |Z_{m1-1}^j - Z_{m1-1}^{j-1}|$$

The magnitude of movement dif1 given by the expression (2) is calculated using m1 data items that represent the positions of source coils started with the source coil located near the distal end of the insertion unit. The calculation of the magnitude of movement dif1 is not limited to the one based on the expression (2). Alternatively, an euclidean distance may be adopted.

A moving distance by which the distal end of the insertion unit has moved, that is, the magnitude of movement dif1 calculated using the expression (2) at step S42 is compared with a predetermined threshold at step S43. If the moving distance that is the magnitude of movement dif1 is larger than the predetermined threshold, it is verified that the distal end of the insertion unit is being inserted. Control is passed to processing started at step S11. If the magnitude of movement is smaller than the threshold, it is verified that the distal end of the insertion unit is at a halt. Processing started at step S44 is executed.

At step S44, similarly to step S42, the PC 15 uses the insertional shape data items relevant to the preceding and current frames to calculate a magnitude of movement dif2, by which the operating unit-side end of the insertion unit of the electronic endoscope 12 has been moved, according to the following expression (3):

$$dif2 = |X_{m-1}^{j} - X_{m-1}^{j-1}| + |X_{m-2}^{j} - X_{m-2}^{j-1}| + \quad \text{[expression 3]}$$
$$|X_{m-3}^{j} - X_{m-3}^{j-1}| + \ldots + |X_{m-m2}^{j} - X_{m-m2}^{j-1}|$$

A moving distance by which the operating unit-side end of the insertion unit has been moved, that is, the magnitude of movement dif 2 calculated based on the expression (3) at step S44 is compared with a predetermined threshold at step S45. If the moving distance that is the magnitude of movement dif2 is smaller than the predetermined threshold, it is verified that the operating unit-side end of the insertion unit is at a halt. Control is passed to processing started at step S11. If the magnitude of movement is larger than the threshold, it is verified that the operating unit-side end of the insertion unit is being moved. Processing started at step S46 is then executed.

Figure 8:
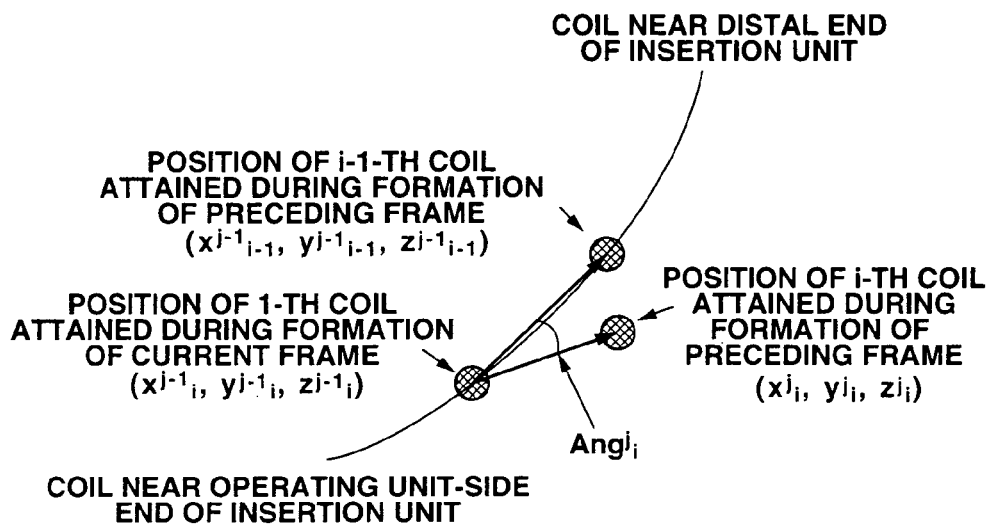
FIG. 8 is an explanatory diagram showing an angle between the orientation of an endoscope insertion unit included in the electronic endoscopic system employing the second embodiment and the direction of the movement made by the insertion unit.

Thereafter, at step S46, as shown in FIG. 8, an angle $Ang_{1}^{j}$ between the direction of the movement made by the distal end of the insertion unit and the previous orientation of the insertion unit is calculated according to an expression (4) by PC 15. Herein, the direction of the movement made by the distal end of the insertion unit is calculated using coordinates that represent the positions of the i-th coil detected during formation of the j-th frame that is a current frame and during formation of the j−1-th frame that is a preceding frame. Moreover, the previous orientation of the insertion unit is calculated using coordinates that represent the positions of the i-th and i−1-th coils detected during formation of the j−1 frame that is the preceding frame.

$$Vec1 = (X_{i}^{j} - X_{i}^{j-1}, Y_{i}^{j} - Y_{i}^{j-1}, Z_{i}^{j} - Z_{i}^{j-1}) \quad \text{[expression 4]}$$
$$= (VX1, VY1, VZ1)$$
$$Vec2 = (X_{i-1}^{j-1} - X_{i}^{j-1}, Y_{i-1}^{j-1} - Y_{i}^{j-1}, Z_{i-1}^{j-1} - Z_{i}^{j-1})$$
$$= (VX2, VY2, VZ2)$$
$$dn1 = \sqrt{VX1^2 + VY1^2 + VZ1^2}$$
$$dn2 = \sqrt{VX2^2 + VY2^2 + VZ2^2}$$
$$Ang_{i}^{j} = \cos^{-1}(VX1\ VX2 + VY1\ VY2 + VZ1\ VZ2)/$$
$$(dn1\ dn2)$$

In other words, the direction of a vector Vec 2 defined with coordinates $(X^{j-1}_{i}, Y^{j-1}_{i}, Z^{j-1}_{i})$ and coordinates $(X^{j-1}_{i-1}, Y^{j-1}_{i-1}, Z^{j-1}_{i-1})$ indicates the previous orientation of the insertion unit. The direction of a vector Vec1 defined with coordinates $(X^{j-1}_{i}, Y^{j-1}_{i}, Z^{j-1}_{i})$ and coordinates $(X^{j}_{i}, Y^{j}_{i}, Z^{j}_{i})$ indicates the direction of the movement made by the distal end of the insertion unit. Herein, i denotes any of the predefined coil numbers.

Thereafter, at step S47, the PC 15 compares the angle $Ang_{1}^{j}$ calculated at step S46 with a predetermined threshold and judges whether the insertion unit of the electronic endoscope 12 has been inserted in a direction corresponding to the previous orientation. If the angle $Ang_{1}^{j}$ between the direction of the movement made by the distal end of the insertion unit and the previous orientation of the insertion unit is smaller than the predetermined threshold, it is judged that an operator is inserting the electronic endoscope 12. Processing started at step S48 is then executed. If the angle $Ang_{1}^{j}$ is larger than the predetermined threshold, it is judged that the electronic endoscope 12 is not inserted. Control is then passed to processing started with step S11.

If it is judged at step S47 that the electronic endoscope 12 is being inserted, the PC 15 judges at step S48 whether the inserted state of the electronic endoscope 12 has continued over a predetermined number of frames. If it is judged that the inserted state has not continued over the predetermined number of frames, control is passed to processing started at step S11. If it is judged that the inserted state has continued over the predetermined number of frames, it is verified that the large intestine has stretched. At step S49, a warning is generated to provide information on the shape of the endoscope insertion unit. The way of warning may be such that the PC 15 generates a warning sound or displays a warning message in the warning indicator section 110 of the examination window shown in FIG. 6. Moreover, the warning indication is not limited to characters but may be an icon or any other graphic. Moreover, the characters or graphic may be flickered.

Consequently, the stretch of the large intestine causing a patient or a subject discomfort can be readily detected.

A description has been made of a case where when the image processing system 4 receives insertional shape data from the insertional shape observing system 3, the stretch of the large intestine is detected and a warning is given. Alternatively, a viewer enabling browsing of an endoscopic image and insertional shape data may be made available, and the stretch of the large intestine may be detected relative to designated insertional shape data.

Figure 9:
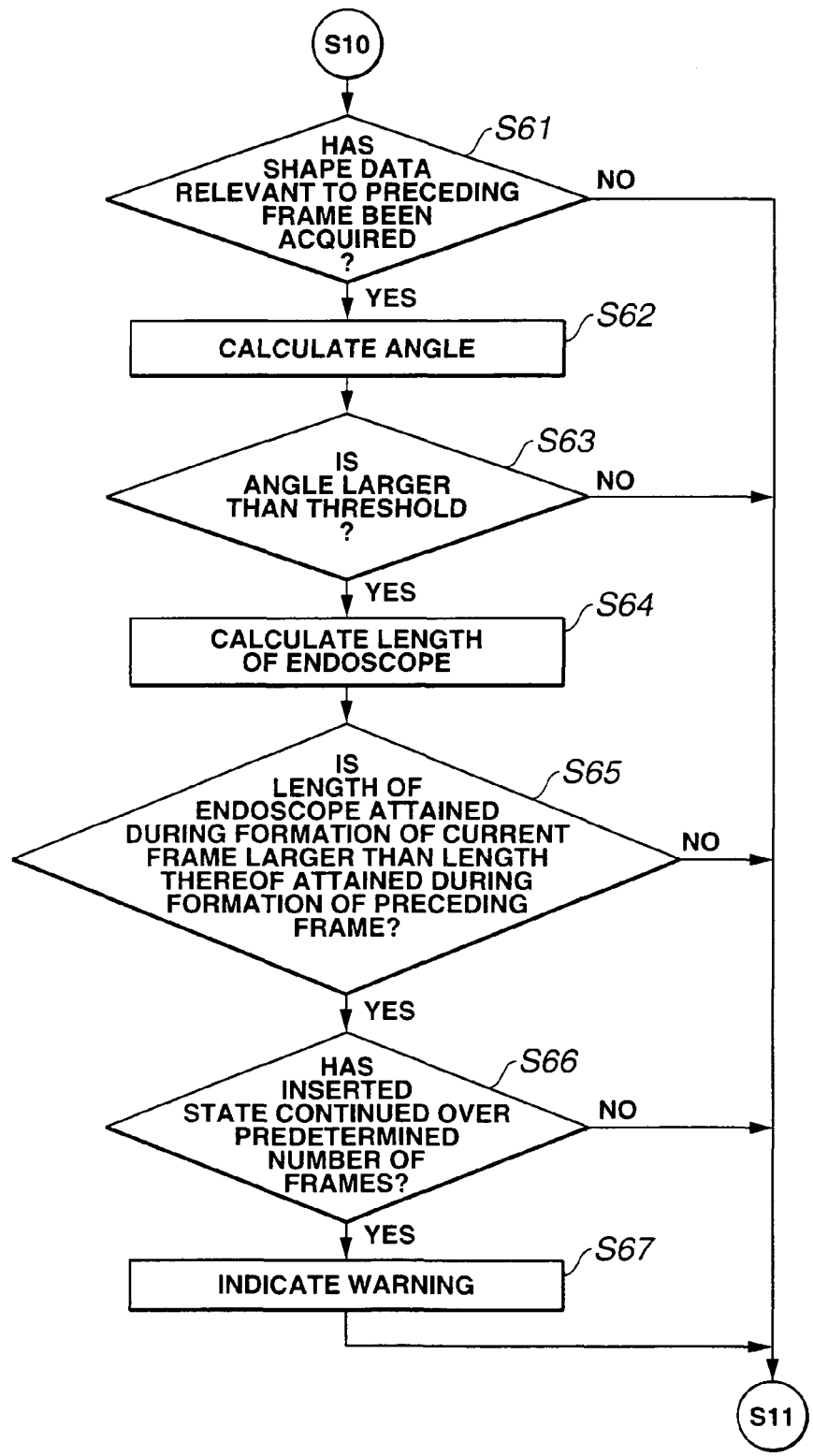
FIG. 9 is a flowchart describing an operation of detecting the angle of a distal endoscope section and giving a warning that is provided by an electronic endoscopic system employing a third embodiment of the present invention.

Next, a third embodiment of the present invention will be described in conjunction with FIG. 9 and FIG. 10.

The configuration of the electronic endoscopic system 1 employing the third embodiment is identical to that of the electronic endoscopic system employing the first embodiment. Moreover, the image processing system 4 treats an endoscopic image or insertional shape data received from the endoscope system 2 and insertional shape-of-endoscope observing system 3 respectively in fundamentally the same manner as that of the first embodiment.

A difference of the third embodiment from the first embodiment lies in detection to be performed when the insertion unit of the electronic endoscope 12 is inserted with the distal part of the insertion unit bent at an angle. If the endoscope insertion unit is inserted with the distal part thereof bent at an angle but the direction of insertion in which the endoscope insertion unit is inserted is not checked, it causes a patient or a subject discomfort. An operator is alerted to insertion performed with the distal part of the endoscope insertion unit bent at an angle.

Detection of insertion performed with the distal part of the endoscope insertion unit bent at an angle is implemented in an examination application installed in the image processing system 4 similarly to that in the image processing system of the first embodiment. When the PC 15 invokes the examination application, the examination window 100 shown in FIG. 6 is opened on the display 18. Actions described in the examination application are identical to those performed at the aforesaid steps S1 to S12. However, warning executed at step S10 is replaced with processing started at step S61 as described in FIG. 9.

At step S61, the PC 15 verifies whether insertional shape data relevant to a frame preceding a current frame that has relevant insertional shape data acquired and preserved at step S8 has been acquired. If it is verified that the insertional shape data relevant to the preceding frame has not been acquired, control is passed to processing started at step S11.

If it is verified at step S61 that the insertional shape data relevant to the preceding frame has been acquired, the PC 15 calculates the angle $Ang^j_1$, at which the distal part of the insertion unit of the electronic endoscope 12 is bent, using the insertional shape data items relevant to the preceding and current frames. The angle $Ang^j_1$ is calculated according to an expression (5) using, as shown in FIG. 10, coordinates that represent the positions of three successive source coils that are selected from among m source coils started with the source coil located near the distal end of the endoscope insertion unit. The larger the angle at which a vector Vec 3 and a vector Vec 4 meet with the initial points thereof matched with each other, the greater the bend of the distal part of the insertion unit.

$$Vec3 = (X^j_i - X^j_{i+1}, Y^j_i - Y^j_{i+1}, Z^j_i - Z^j_{i+1}) \quad \text{[expression 5]}$$
$$= (VX3, VY3, VZ3)$$
$$Vec4 = (X^j_{i+2} - X^j_{i+1}, Y^j_{i+2} - Y^j_{i+1}, Z^j_{i+2} - Z^j_{i+1})$$
$$= (VX4, VY4, VZ4)$$
$$dn3 = \sqrt{VX3^2 + VY3^2 + VZ3^2}$$
$$dn4 = \sqrt{VX4^2 + VY4^2 + VZ4^2}$$
$$Ang^j_i = \cos^{-1}(VX3\ VX4 + VY3\ VY4 + VZ3\ VZ4)/$$
$$(dn3\ dn4)$$

Thereafter, at step S63, the PC 15 compares the plurality of angles $Ang^j_1$ calculated at step S62 with a predetermined threshold. If any of the angles $Ang^j_1$ is larger than the predetermined threshold, it is judged that the distal part of the endoscope insertion unit is angled. Processing started at step S64 is then executed. If it is judged that none of the calculated angles $Ang^j_1$ is larger than the predetermined threshold, control is passed to processing started at step S11.

If it is judged at step S63 that any of the calculated angles $Ang^j_1$ is larger than the predetermined threshold and the distal part of the endoscope insertion unit is angled, the PC 15 calculates the length of the insertion unit of the electronic endoscope 12 that is attained during formation of the current frame and that is sensed by the shape processing unit 13 included in the inserted-form observing system 3. The length of the insertion unit of the electronic endoscope 12 is calculated based on the number of effective sets of coordinates that represent the positions of source coils and that are specified in the insertional shape data produced by the shape processing unit 13.

Thereafter, at step S65, the PC 15 compares the length of the insertion unit attained during formation of the current frame and calculated at step S64 with the length of the endoscope insertion unit attained during formation of the frame preceding the current frame. If the result of the comparison performed at step S65 demonstrates that the length of the endoscope insertion unit attained during formation of the current frame is larger than the length thereof attained during formation of the preceding frame, it is verified that the insertion unit is being inserted into the deep region of an organ. Control is then passed to processing started at step S66. If the length of the endoscope insertion unit attained during formation of the current frame is smaller than the length thereof attained during formation of the preceding frame, it is verified that the insertion unit is at a halt or being pulled. Processing started at step S11 is then executed.

The PC 15 verifies at step S66 whether the increase in the length of the endoscope insertion unit has continued over a predetermined number of frames.

If it is verified at step S66 that the increase in the length of the insertion unit has not continued over the predetermined number of frames, control is passed to processing started at step S11. If it is verified that the increase in the length of the insertion unit has continued over the predetermined number of frames, a warning signal is produced at step S67 in order to warn that the endoscope insertion unit is being inserted with the distal part thereof angled. Information on the shape of the endoscope insertion unit may be provided or a warning sound may be generated. Otherwise, a warning message may be displayed in the warning indicator section 110 of the examination window 100 shown in FIG. 6. The warning indication is not limited to characters but may be an icon or any other graphic. Moreover, the characters or graphic may be flickered.

Consequently, using a plurality of insertional shape data items relevant to a current frame and a preceding frame, information on the shape of the endoscope insertion unit can be provided according to the movement of the actually inserted endoscope insertion unit. Insertion of the endoscope insertion unit with the distal part thereof angled, which causes a patient discomfort, can be detected, and a warning can be given. Otherwise, a viewer permitting browsing of an image and shape data may be made available, and a warning that the insertion unit is being inserted with the distal part thereof angled may be given based on designated insertional shape data.

Figure 12:
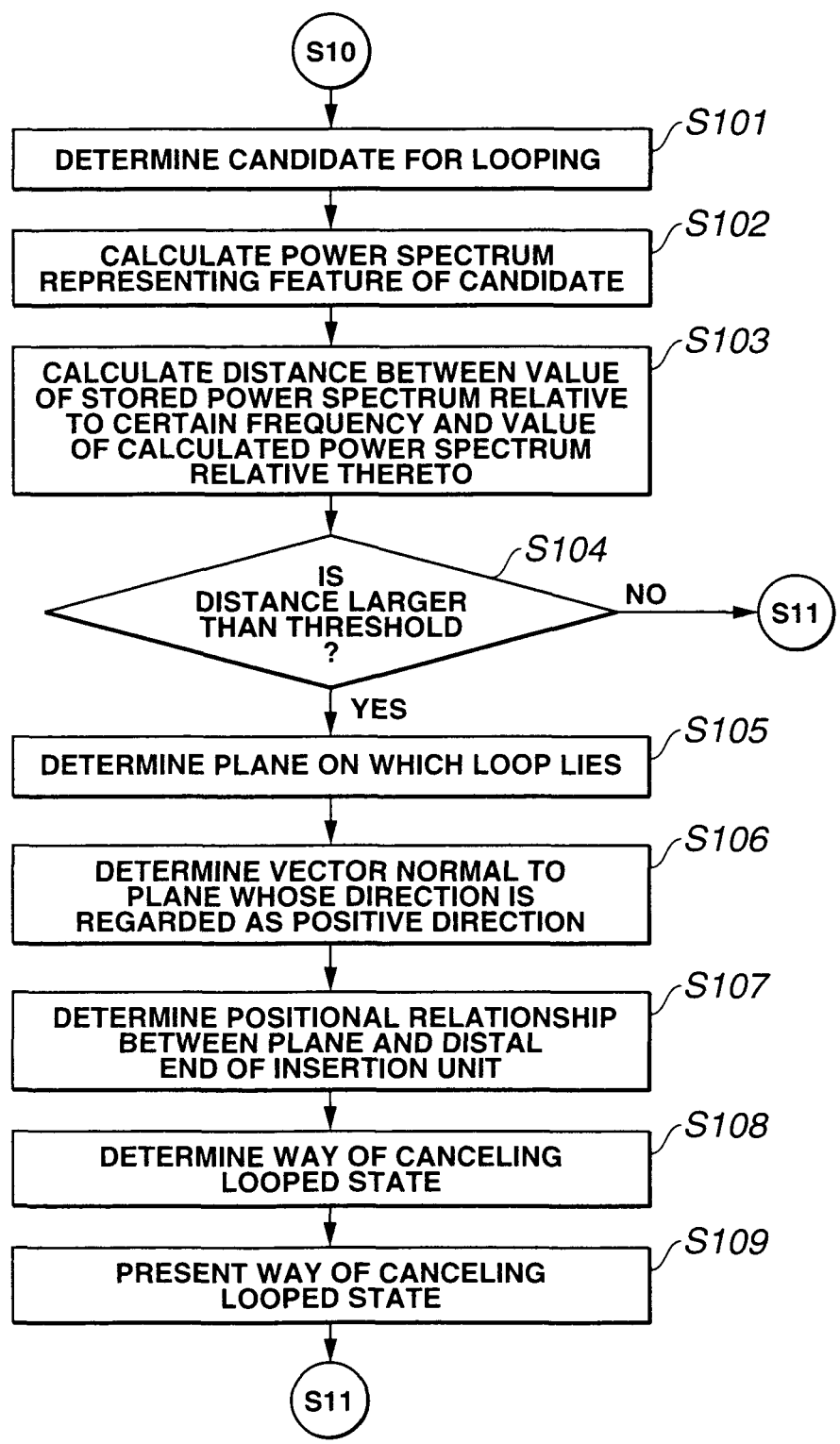
FIG. 12 is a flowchart describing an operation of detecting a looped endoscope insertion unit and presenting a way of canceling the looped state that is provided by an electronic endoscopic system employing a fifth embodiment of the present invention.
Figure 13:
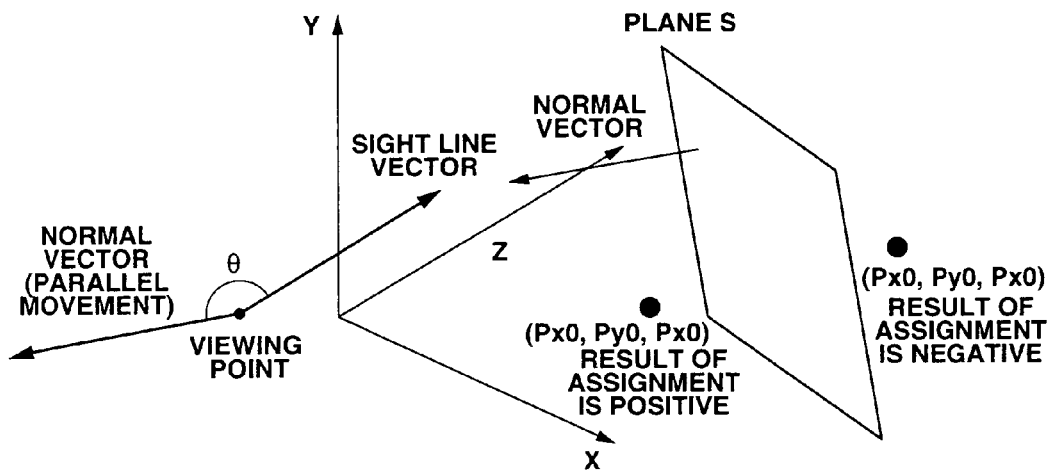
FIG. 13 is an explanatory diagram showing the looped state of the endoscope insertion unit included in the electronic endoscopic system employing the fifth embodiment.
Figure 14:
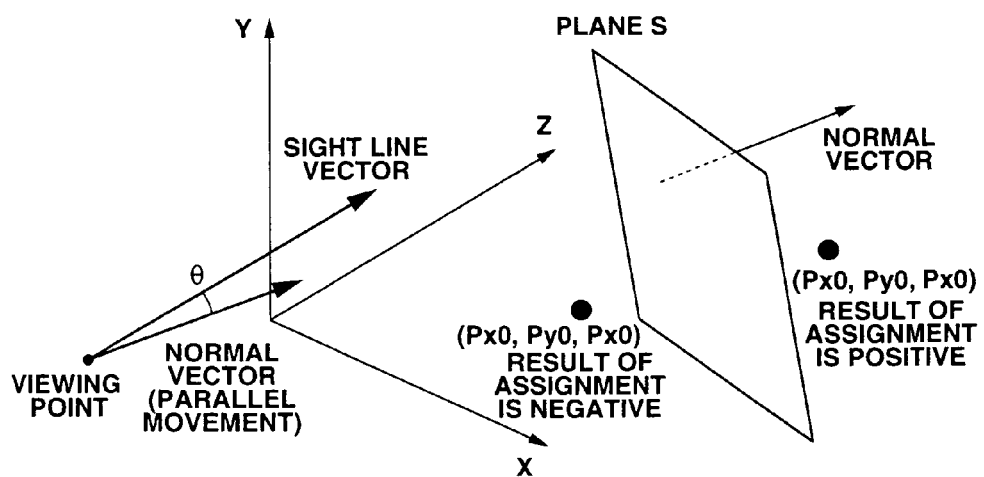
FIG. 14 is an explanatory diagram showing the looped state of the endoscope insertion unit included in the electronic endoscopic system employing the fifth embodiment.

Next, a fourth embodiment of the present invention will be described in conjunction with FIG. 11 and FIG. 12.

The configuration of the electronic endoscopic system 1 employing the fourth embodiment is identical to that of the electronic endoscopic system employing the first embodiment. Moreover, the image processing system 4 treats an endoscopic image and insertional shape data, which are received from the endoscope system 2 and insertional shape-of-endoscope observing system 3 respectively, in fundamentally the same manner as that of the first embodiment.

The fourth embodiment is different from the third embodiment in a point that insertion of the insertion unit of the electronic endoscope 12 performed with the distal part thereof angled in a different manner is detected.

Detection of insertion performed with the distal part of the endoscope insertion unit angled is implemented in an examination application to be installed in the image processing system 4 similarly to that in the image processing system of the third embodiment. When the PC 15 invokes the examination application, the examination window 100 shown in FIG. 6 is opened on the display 18. Actions described in the examination application are identical to those performed at the aforesaid steps S1 to S12. However, processing executed at step S10 is replaced with the one started at step S81 as described in FIG. 11.

At step S81, the PC 15 verifies whether insertional shape data relevant to a frame preceding a current frame that has relevant insertional shape data acquired and recorded at step S8 has been acquired. If it is verified that the insertional shape data relevant to the preceding frame has not been acquired. Control is passed to processing started at step S11.

Figure 10:
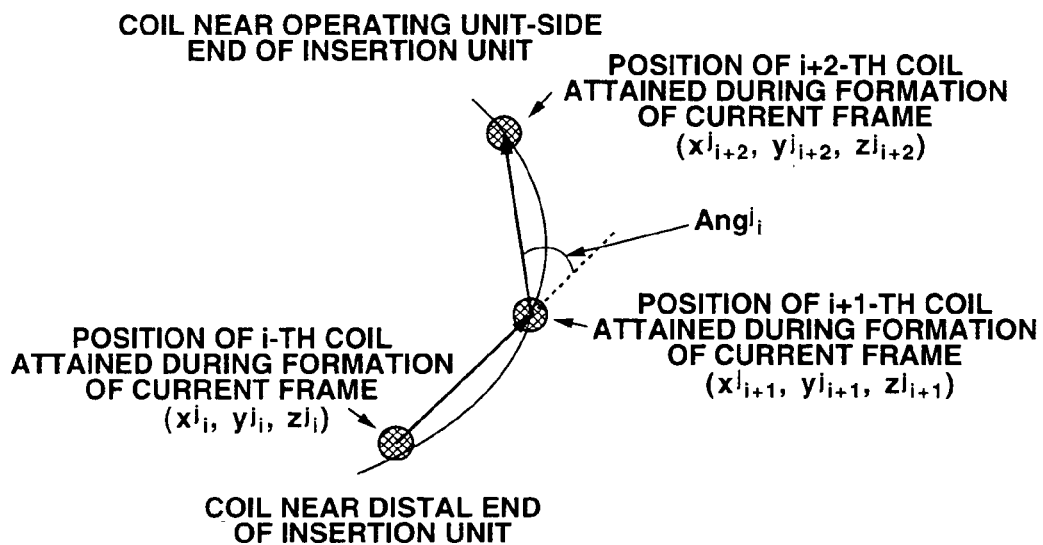
FIG. 10 is an explanatory diagram concerning detection of the angle of the distal endoscope section performed in the electronic endoscopic system employing the third embodiment.

If it is verified at step S81 that the insertional shape data relevant to the preceding frame has been acquired, the PC 15 calculates at step S82 the angle $Ang^j_1$, at which the distal part of the insertion unit of the electronic endoscope 12 is bent, using the insertional shape data items relevant to the preceding and current frames according to the expression (5) as shown in FIG. 10. Specifically, the angle $Ang^j_1$ is calculated using coordinates that represent the positions of three successive source coils that are selected from among m source coils started with the source coil located near the distal end of the endoscope insertion unit.

Thereafter, at step S83, the PC 15 compares a plurality of angles $Ang^j_1$ calculated at step S82 with a predetermined threshold. If any of the angles $Ang^j_1$ is larger than the predetermined threshold, it is judged that the distal part of the endoscope insertion unit is angled. Processing started at step S84 is then executed. If it is judged that none of the angles $Ang^j_1$ is larger than the predetermined threshold, control is passed to processing started at step S11.

If it is judged at step S83 that any of the angles $Ang^j_1$ is larger than the predetermined threshold and the distal part of the endoscope insertion unit is angled, as shown in FIG. 8, the PC 15 calculates at step S84 according to the expression (4) an angle between the direction of the movement made by the operating unit-side part of the insertion unit of the electronic endoscope 12, and the orientation of the operating unit-side part thereof. Specifically, the angle $Ang^j_1$ between the direction of the movement made by the operating unit-side part of the insertion unit and the orientation of the operating unit-side part thereof is calculated. At this time, the direction of the movement made by the operating unit-side part of the insertion unit is calculated using coordinates that represent the positions of the i-th coil detected during formation of the j-th frame that is a current frame and the j−1-th frame that is a preceding frame. The orientation of the operating unit-side part thereof is calculated using coordinates that represent the positions of the i-th and i+1-th coils detected during formation of the j−1 frame that is the preceding frame.

Referring to FIG. 8, the direction of a vector Vec2 defined with coordinates $(X^{j-1}_i, Y^{j-1}_i, Z^{j-1}_i)$ and coordinates $(X^{j-1}_{i-1}, Y^{j-1}_{i-1}, Z^{j-1}_{i-1})$ indicates the orientation of the insertion unit. The direction of a vector Vec 1 defined with coordinates $(X^{j-1}_i, Y^{j-1}_i, Z^{j-1}_i)$ and coordinates $(X^j_i, Y^j_i, Z^j_i)$ indicates the direction of the movement made by the distal part of the insertion unit. Herein, i denotes any of the predefined coil numbers.

At step S85, the PC 15 compares the angle $Ang^j_1$ calculated at step S84 with a predetermined threshold so as to judge whether the operating unit-side part of the insertion unit of the electronic endoscope 12 has been inserted. If the angle $Ang^j_1$ between the direction of the movement made by the operating unit-side part of the insertion unit and the orientation of the operating unit-side part thereof is smaller than predetermined threshold, it is judged that an operator is inserting the operating unit-side part of the insertion unit of the electronic endoscope 12. Processing started at step S86 is then executed. If the angle $Ang^j_1$ is larger than the predetermined threshold, it is judged that the operating unit-side part of the insertion unit of the electronic endoscope 12 is not inserted. Control is then passed to processing started at step S11.

If it is judged at step S85 that the operating unit-side part of the insertion unit of the electronic endoscope 12 is being inserted, the PC 15 calculates an angle $Ang^j_1$ between the direction of the movement made by the distal part of the insertion unit and the orientation of the insertion unit according to the expression (4) at step S86. Herein, the direction of the movement made by the distal part of the insertion unit is calculated, as shown in FIG. 8, using coordinates that represent the positions of the i-th coil detected during formation of the j-th frame, that is, a current frame and during formation of the j−1-th frame, that is, a preceding frame. The orientation of the insertion unit is calculated using coordinates that represent the positions of the i-th coil and i+1-th coil detected during formation of the j−1-th frame, that is, the preceding frame.

Referring to FIG. 8, the direction of a vector Vec 2 defined with coordinates $(X^{j-1}_i, Y^{j-1}_i, Z^{j-1}_i)$ and coordinates $(X^{j-1}_{i-1}, Y^{j-1}_{i-1}, Z^{j-1}_{i-1})$ indicates the orientation of the insertion unit. The direction of a vector Vec1 defined with coordinates $(X^{j-1}_i, Y^{j-1}_i, Z^{j-1}_i)$ and coordinates $(X^j_i, Y^j_i, Z^j_i)$ indicates the direction of the movement made by the distal part of the insertion unit. Herein, i denotes any of the predefined coil numbers.

Thereafter, at step S87, the PC 15 judges from the angle $Ang^j_1$ calculated at step S86 whether the distal part of the insertion unit of the electronic endoscope 12 is inserted in a direction different from a direction of observation. As for the judgement of the direction of the movement made by the distal part of the insertion unit, if the angle $Ang^j_1$ defined with the orientation of the distal part of the insertion unit is larger than a predetermined threshold, it is judged that the distal part of the endoscope insertion unit is inserted in a direction different from the direction of observation. If it is judged at step S87 that the distal part of the endoscope insertion unit is inserted in the direction different from the direction of observation, processing started at step S88 is executed. If it is judged that the distal part of the endoscope insertion unit is inserted in the direction of observation, control is passed to processing started at step S11.

If it is judged at step S87 that the distal part of the endoscope insertion unit is inserted in the direction different from the direction of observation, the PC 15 judges whether the insertion in the direction different from the direction of observation has continued over a predetermined number of frames. If it is judged that the insertion has not continued over the predetermined number of frames, control is passed to processing started at step S11. If it is judged that the insertion has continued over the predetermined number of frames, it is verified that the distal part of the insertion unit is inserted while being angled by handling the operating unit of the endoscope. At step S89, a warning is given. The way of warning may be such that the PC 15 generates a warning sound or displays a warning message in the warning indicator section 110 of the examination window 100 shown in FIG. 6. Moreover, the warning indication is not limited to characters but may be an icon or any other graphic. Moreover, the characters or graphic may be flickered.

Consequently, insertion performed with the distal end of the insertion unit angled, which causes a patient or a subject uneasiness, can be readily detected.

A description has been made of a case where when the image processing system 4 receives insertional shape data from the insertional shape observing system 3, insertion with the distal part of the insertion unit angled is detected and a warning is given. A viewer permitting browsing of an endoscopic image and insertional shape data may be made available, and a warning may be given based on designated insertional shape data.

Next, a fifth embodiment of the present invention will be described in conjunction with FIG. 12 to FIG. 18.

The configuration of the electronic endoscopic system 1 employing the fifth embodiment is identical to that of the electronic endoscopic system employing the first embodiment. Moreover, the image processing system 4 treats an endoscopic image and insertional shape data, which are received from the endoscope system 2 and insertional shape-of-endoscope observing system 3 respectively, in fundamentally the same manner as that of the first embodiment.

For example, while the insertion unit of a colonoscope is being inserted into the large intestine, the insertion unit may be looped. The loop falls into an α loop, an N loop, or a γ loop according to the shape.

In order to alleviate uneasiness which the loop causes a patient or a subject or in order to improve the ease of insertion of the insertion unit, the looped endoscope insertion unit is restored to the original state and straightened.

When the endoscope insertion unit is looped while being inserted, the looped state is recognized and indicated. Moreover, the way of straightening the endoscope insertion unit is presented. Thus, the ease of insertion of the endoscope insertion unit is improved, the time required for endoscopic examination is shortened, and patient discomfort is alleviated.

Detection of the looped distal part of the endoscope insertion unit is implemented in an examination application installed in the image processing system 4 similarly to that installed in the first embodiment. When the PC 15 invokes the examination application, the examination window 100 shown in FIG. 6 is opened on the display 18. Actions described in the examination application are identical to those performed at steps S1 to S12. However, processing to be executed at step S10 is replaced with processing started at step S101 as described in FIG. 12.

In order to recognize the looped state of the endoscope insertion unit and straighten the endoscope insertion unit, the fifth embodiment checks if (1) the endoscope insertion unit is looped clockwise or counterclockwise. Herein, the direction of looping shall be a direction from the distal end of the endoscope insertion unit towards the operating unit-side end thereof. Moreover, it is checked (2) whichever of the distal-end side of the looped portion of the endoscope insertion unit and the operating-unit side thereof is located near a viewing point.

The insertional shape of the endoscope may be regarded as a curve. For recognition of a loop and verification of the direction of looping, a feature-of-curve extraction technology can be utilized.

For brevity's sake, the present embodiment will be described on the assumption that an insertional shape is a quadratic curve projected on an XY plane and characterized with, for example, a P-type Fourier descriptor. For the P-type Fourier description, refer to the journal published by the Institute of Electronics, Information and Communication Engineers (Vol. j67-A, No. 3).

According to the technique employed in the present embodiment, a curve is divided into Vn (where Vn denotes a positive number equivalent to a divisor) segments, and the limits of the segments are represented with complex numbers. A function of a total curvature at each of the limits is defined and Fourier-transformed, whereby a power spectrum is calculated. The power spectrum is thought to represent the feature of the curve.

On the other hand, the features of loops shaped like clockwise and counterclockwise circles are characterized with P-type Fourier descriptors, and the P-type Fourier descriptors are stored in advance. Accordingly, a power spectrum Cq(k) (where k denotes 0, etc., or Vn−1) is defined to represent the feature of each of the loops. Herein, when q equals 0, the power spectrum represents the feature of a clockwise circular loop. When q equals 1, the power spectrum represents the feature of a counterclockwise circular loop.

At step S101, the PC 15 selects a candidate for looping. When a circular loop is formed, adjoining ones of the source coils are close to each other. If the distance between two adjoining source coils is smaller than a predetermined threshold, a curve defined with the two source coils is determined as a candidate for looping.

Thereafter, at step S102, the PC 15 divides the curve determined as a candidate for looping into Vn segments. A P-type Fourier descriptor characterizing the curve is retrieved and an associated power spectrum C(k) (where k denotes 0, etc., or Vn−1) is obtained. The limits of Vn segments shall be represented with coordinates (Px0, Py0, Pz0), etc., and (PxVn, PyVn, PzVn) in that order with the one located near the distal end of the insertion unit as the first one. The P-type Fourier descriptor specifies x- and y-coordinates alone.

At step S103, the PC 15 calculates a distance defined in the euclidean space between a value of the power spectrum Cq(k) relative to a certain frequency and a value of the power spectrum C(k) relative to the same frequency. The euclidean distance calculated at step S103 is compared with a predetermined threshold at step S104. If the calculated euclidean distance is smaller than the threshold, it is judged that a loop is formed. In the judgment whether a loop is formed, if an euclidean distance between a value of the power spectrum C0(k) relative to a certain frequency and a value of the power spectrum C(k) relative to the same frequency is smaller than the threshold, and an euclidean distance between a value of the power spectrum C1(k) relative to the frequency and a value of the power spectrum C(k) relative thereto is also smaller than the threshold, it is judged that the direction of looping is determined with the smaller one of the values of the power spectra C0(k) and C1(k). If no loop is formed, control is passed to processing started at step S11.

If it is judged at step S104 that the insertion unit is looped, the PC 15 determines a plane S, on which the insertion unit is looped, using coordinates (Pxvn, Pyvn, PzVn), (PxVn−1, PyVn−1, PzVn−1), and (PxVn−2, PyVn−2, PzVn−2) at step S105. Thereafter, at step S106, a vector normal to the plane S is determined, and an angle θ between the normal vector and a sight line vector whose direction represents the direction in which the endoscope insertion unit is viewed is calculated. At step S107, coordinates (Px0, Py0, Pz0) representing the position of a limit located near the distal end of the insertion unit are assigned to a formula defining the plane S. Thus, it is determined whether the position of the limit lies near the viewing point beyond the plane S or away from the viewing point beyond the plane S.

In order to judge whether the position of the limit lies near the viewing point beyond the plane S or away from the viewing point, it is verified whether the angle θ is larger than 90° and the result of the assignment is positive. Namely, (1) if the angle θ is larger than 90° and the result of the assignment is positive, the position of the limit lies near the viewing point (see FIG. 13). (2) If the angle θ is larger than 90° and the result of the assignment is negative, the position of the limit lies away from the viewing point (see FIG. 13). (3) If the angle θ is equal to or smaller than 90° and the result of the assignment is positive, the position of the limit lies away from the viewing point (see FIG. 14). (4) If the angle θ is equal to or smaller than 90° and the result of the assignment is negative, the position of the limit lies near the viewing point (see FIG. 14).

Based on the direction of looping and the relationship between the distal end of the insertion unit and the plane S which are detected at step S107, a way of handling the endoscope, that is, a way of canceling the looped state is determined at step S108. An example of criteria for determining the way of canceling the looped state is described below.

Figure 15:
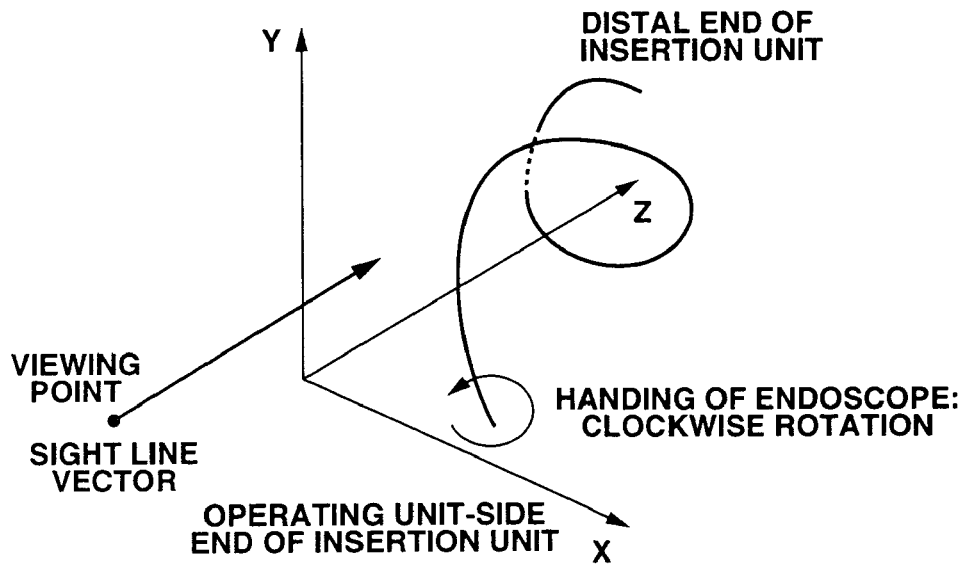
FIG. 15 is an explanatory diagram showing a way of canceling the looped state of the endoscope insertion unit included in the electronic endoscopic system employing the fifth embodiment.
Figure 16:
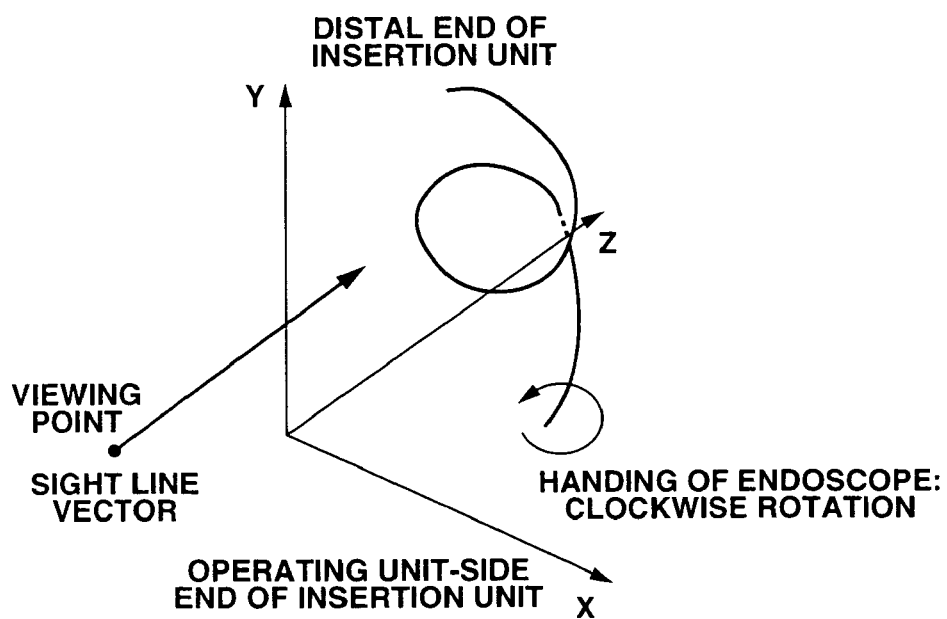
FIG. 16 is an explanatory diagram showing a way of canceling the looped state of the endoscope insertion unit included in the electronic endoscopic system employing the fifth embodiment.
Figure 17:
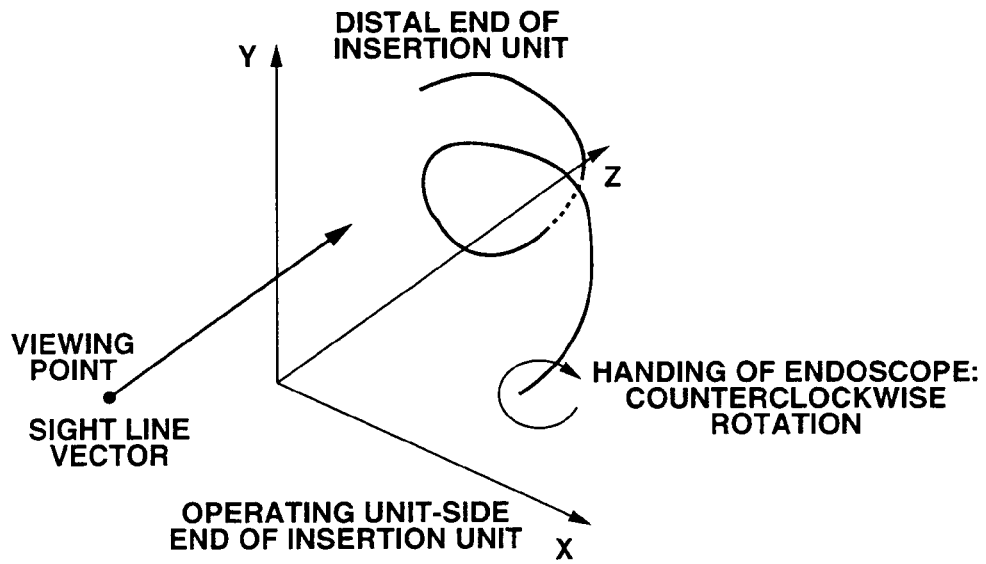
FIG. 17 is an explanatory diagram showing a way of canceling the looped state of the endoscope insertion unit included in the electronic endoscopic system employing the fifth embodiment.
Figure 18:
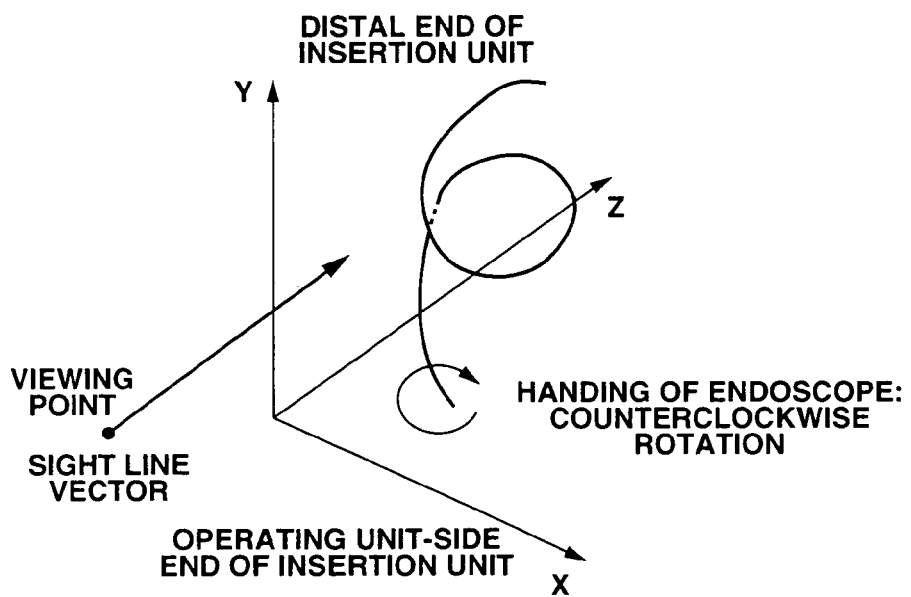
FIG. 18 is an explanatory diagram showing a way of canceling the looped state of the endoscope insertion unit included in the electronic endoscopic system employing the fifth embodiment.

(1) If the insertion unit is looped counterclockwise and the distal part thereof is located away from the viewing point, the endoscope should be rotated clockwise (see FIG. 15). (2) If the insertion unit is looped clockwise and the distal part thereof is located near the viewing point, the endoscope should be rotated clockwise (see FIG. 16). (3) If the insertion unit is looped clockwise and the distal part thereof is located away from the viewing point, the endoscope should be rotated counterclockwise (see FIG. 17). (4) If the insertion unit is looped counterclockwise and the distal part thereof is located near the viewing point, the endoscope should be rotated counterclockwise (see FIG. 18).

Thereafter, at step S109, the PC 15 presents the way of canceling the looped state determined at step S108 as information on handling of the endoscope (information for assisting in handling) in a way-of-handling indicator section 111 of the examination window 100.

Incidentally, in the way-of-handling indicator section 111, as shown in FIG. 6, a graphic or an icon that is an arrow or the like expressing clockwise or counterclockwise rotation of an endoscope, or words describing a way of handling may be presented. Otherwise, an audio directive may be given.

The way of handling the endoscope so as to cancel a looped state has been described to be presented on the assumption that the image processing system 4 receives insertional shape data from the insertional shape observing system 3. A viewer permitting browsing of an endoscopic image and insertional shape data may be made available, and the same presentation may be performed based on designated insertional shape data.

As mentioned above, an insertional shape is recognized, a looped state is recognized and presented, and a way of insertion is suggested. This contributes to improvement in the ease of insertion of an endoscope, shortening of the time required for endoscopic examination, and alleviation of patient pain.

The image processing system 4 of any of the aforesaid first to fifth embodiments may be provided as one of the facilities constituting the electronic endoscopic system 1 or may be integrated into the insertional shape-of-endoscope observing system 3. Moreover, the image processing system 4 may be provided as an integrated system including the insertional shape observing system 3 and electronic endoscopic system 1.

Furthermore, in the first to fifth embodiments, the feature for inferring the shape of the endoscope insertion unit comprises a group of source coils that induces a magnetic field and a group of sense coils that detects the magnetic field. Herein, either of the groups of source coils and sense coils is incorporated in the endoscope insertion unit. The shape of the insertion unit is inferred from the magnetic field detected by the group of sense coils. Alternatively, for example, an optical fiber that causes a transmission loss when being bent may be adopted and run through the endoscope insertion unit. The degree of bending to which the insertion unit is bent may be detected based on a change in an amount of light traveling along the optical fiber. Otherwise, a flexible circuit board may be coated with a special type of ink. The property of the ink whose resistance varies depending on the degree of bending to which the circuit board is bent may be utilized. Any other detecting method may be adopted.

Next, a sixth embodiment of the present invention will be described in conjunction with FIG. 19 to FIG. 24.

Figure 19:
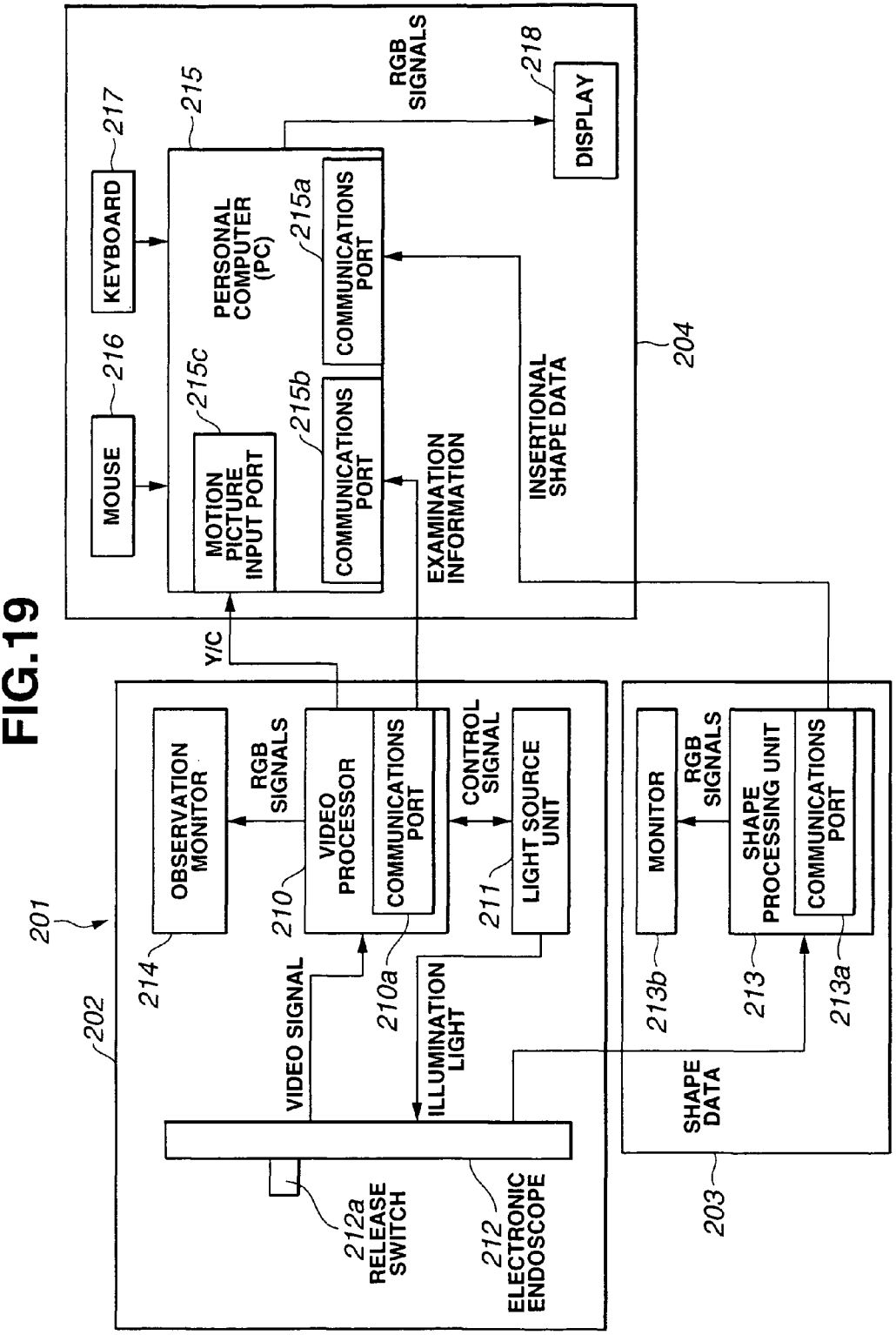
FIG. 19 is a block diagram showing the configuration of an electronic endoscopic system employing a sixth embodiment of the present invention.
Figure 20:
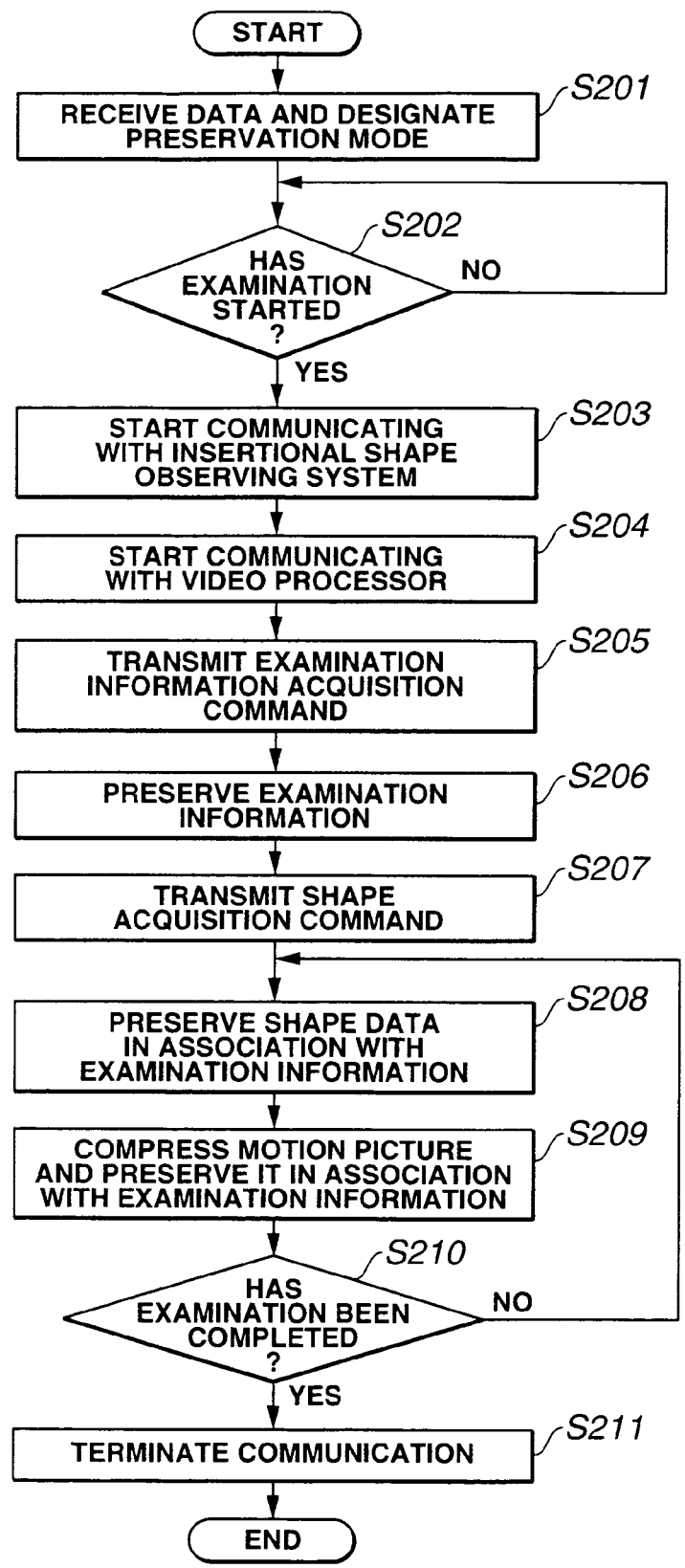
FIG. 20 is a flowchart describing a process of recording or preserving endoscopic image data and insertional shape-of-endoscope data that is executed in the electronic endoscopic system employing the sixth embodiment.
Figure 21:
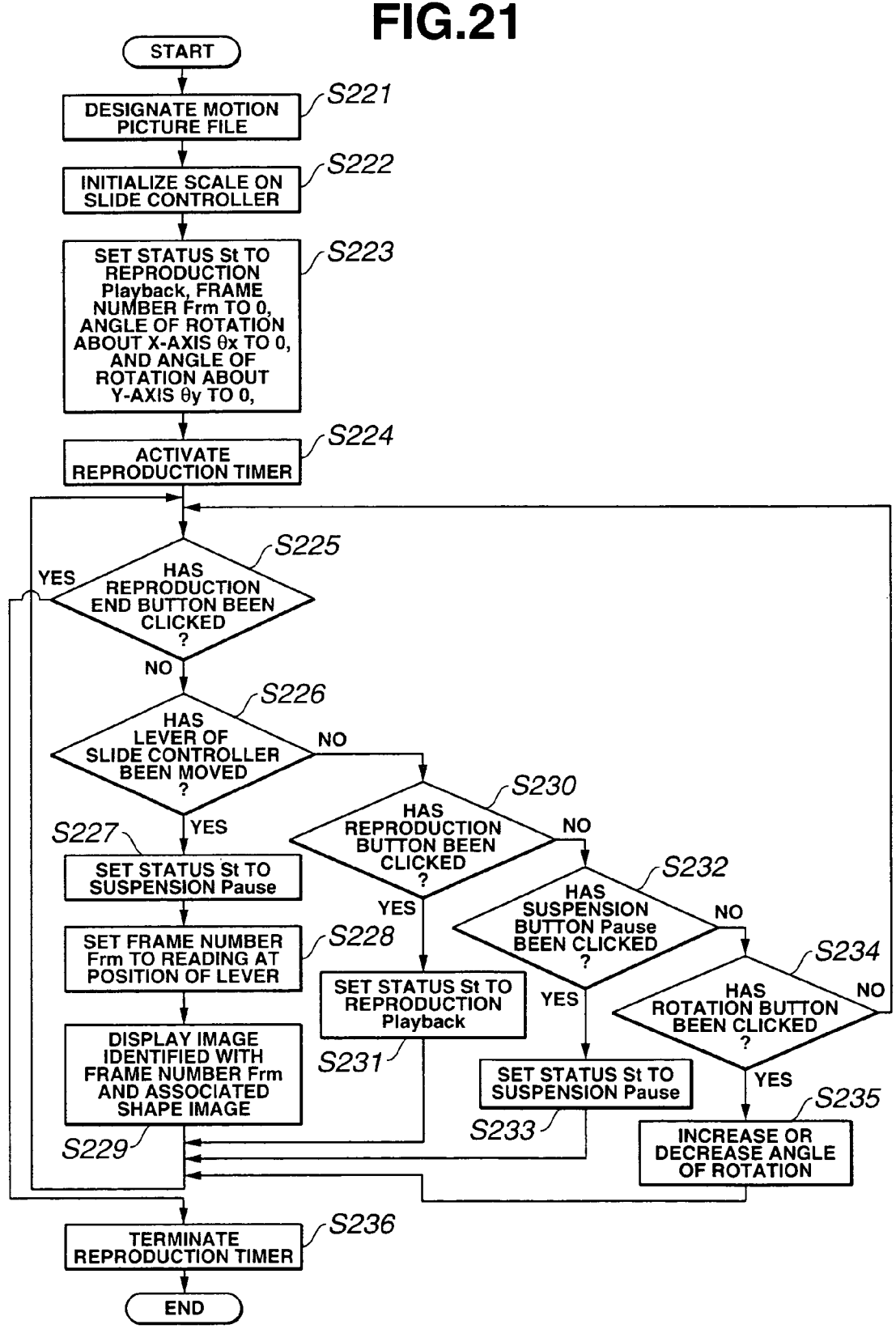
FIG. 21 is a flowchart describing synchronous reproduction of an endoscopic image and an insertional shape-of-endoscope image that is executed in the electronic endoscopic system employing the sixth embodiment.
Figure 22:
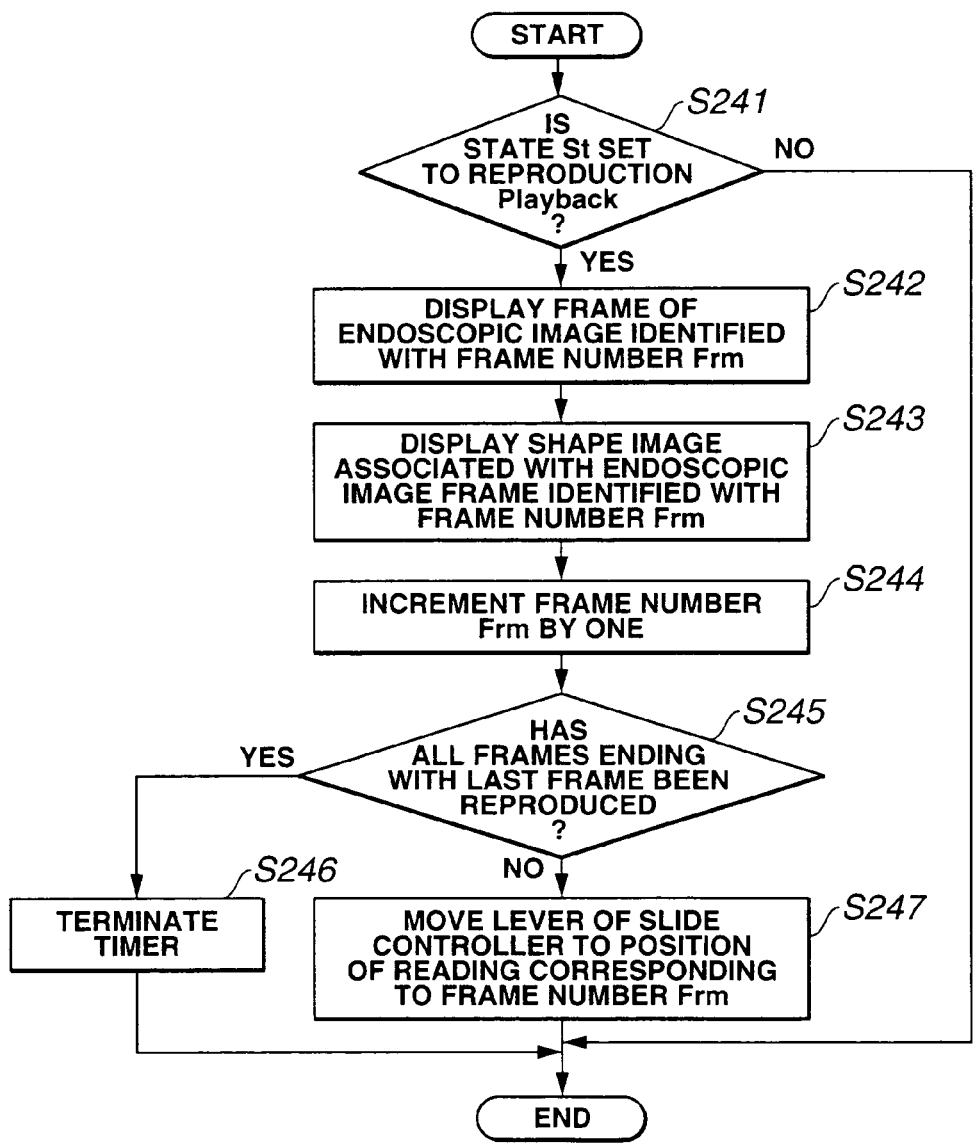
FIG. 22 is a flowchart describing the action of a reproduction timer in synchronous reproduction of an endoscopic image and an insertional shape-of-endoscope image that is employed in the electronic endoscopic system employing the sixth embodiment.
Figure 23:
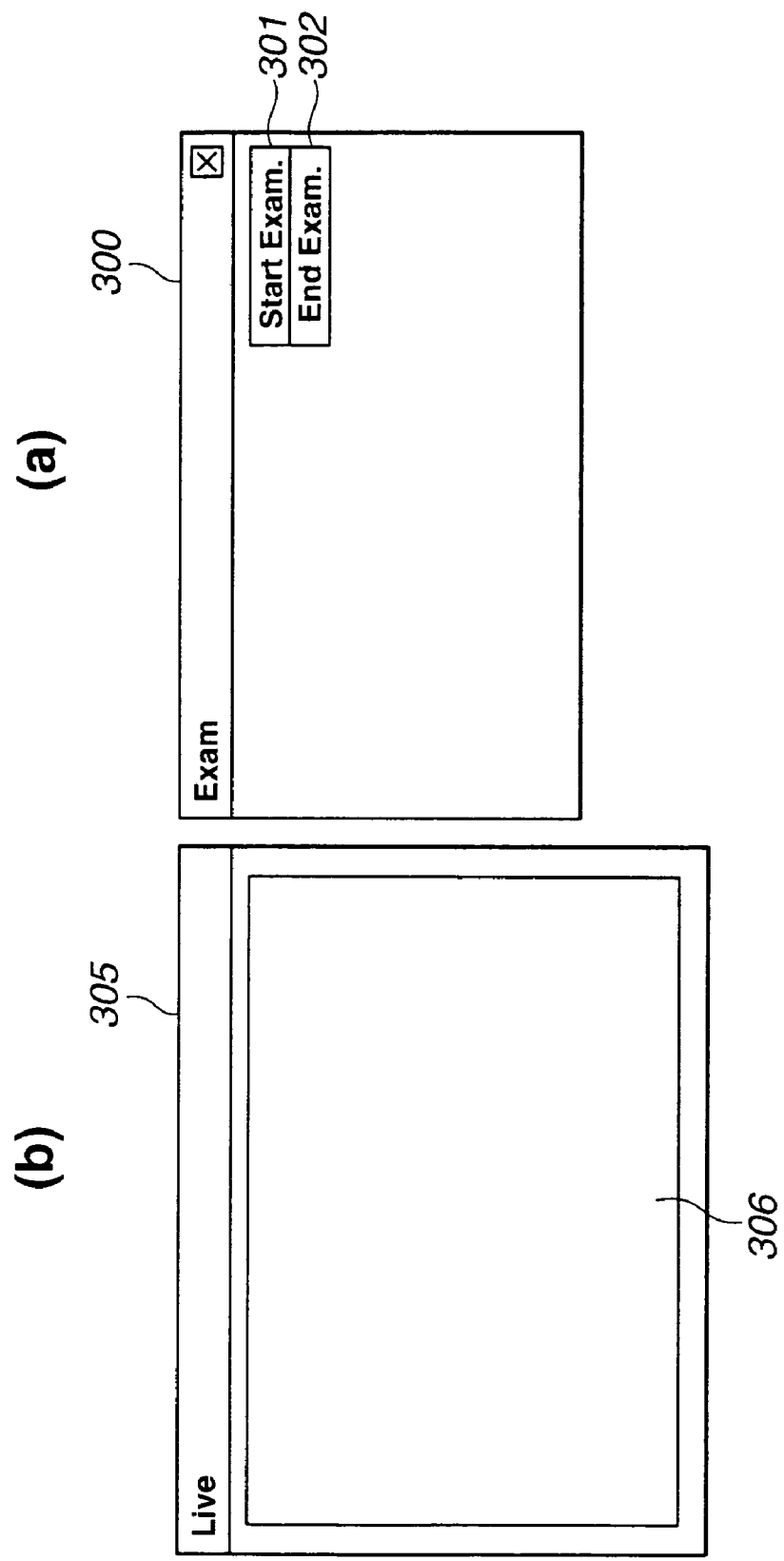
FIG. 23 shows display screen images displayed during recording or preservation of an endoscopic image and insertional shape-of-endoscope data that is performed in the electronic endoscopic system employing the sixth embodiment.
Figure 24:
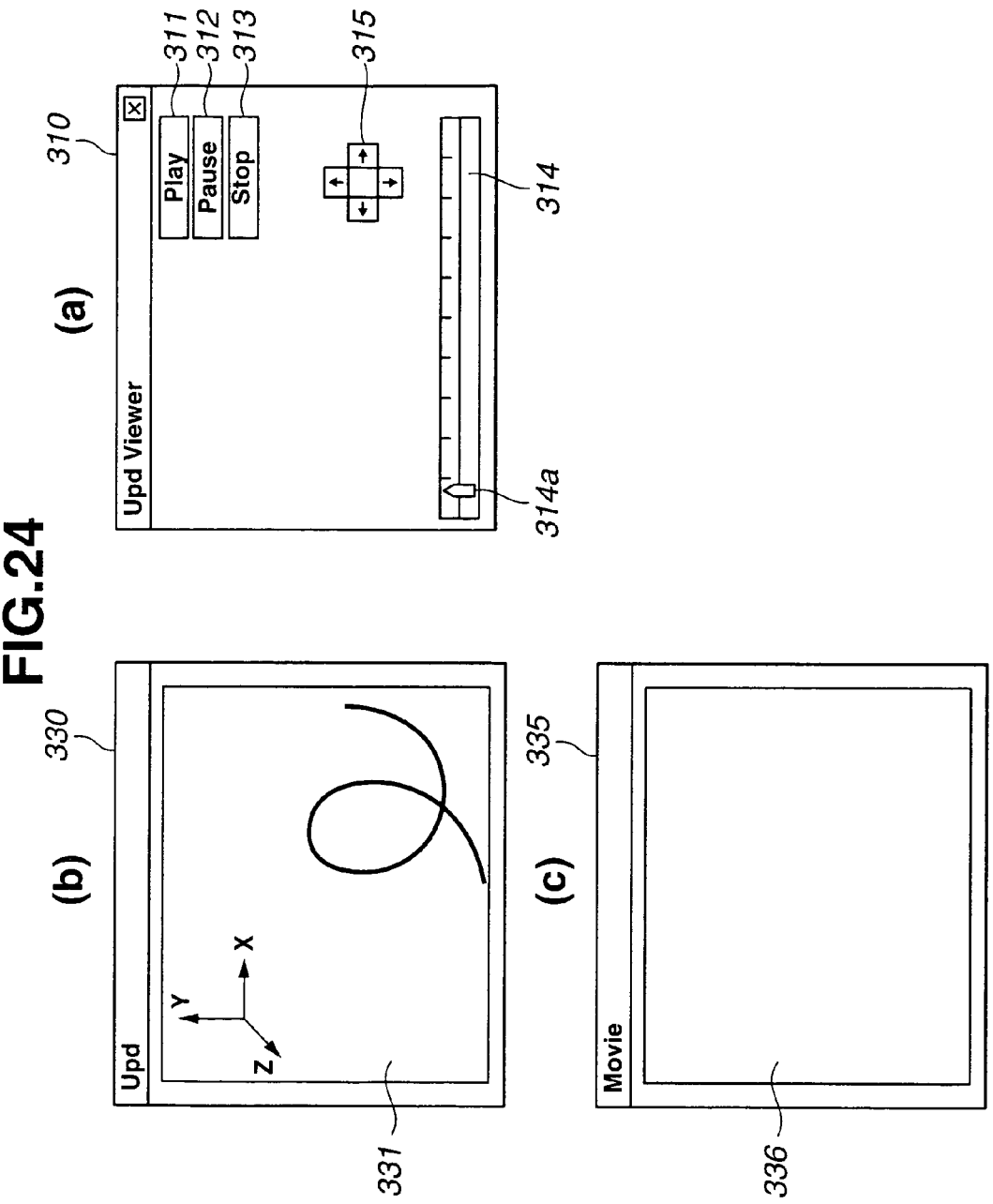
FIG. 24 shows display screen images displayed during synchronous reproduction of an endoscopic image and an insertional shape-of-endoscope image that is performed in the electronic endoscopic system employing the sixth embodiment.

FIG. 19 is a block diagram showing the configuration of an electronic endoscopic system employing the sixth embodiment of the present invention. FIG. 20 is a flowchart describing a process of recording or preserving an endoscopic image and insertional shape-of-endoscope data that is executed in the electronic endoscopic system employing the sixth embodiment. FIG. 21 is a flowchart describing synchronous reproduction of an endoscopic image and an insertional shape-of-endoscope image that is executed in the electronic endoscopic system employing the sixth embodiment. FIG. 22 is a flowchart describing the action of a reproduction timer enabling synchronous reproduction of an endoscopic image and an insertional shape-of-endoscope image that is implemented in the electronic endoscopic system employing the sixth embodiment. FIG. 23 shows a display screen image to be displayed when an endoscopic image and insertional shape-of-endoscope data are recorded or preserved in the electronic endoscopic system employing the sixth embodiment. FIG. 24 shows a display screen image to be displayed during synchronous reproduction of an endoscopic image and an insertional shape-of-endoscope image in the electronic endoscopic system employing the sixth embodiment.

To begin with, an electronic endoscopic system 201 employing an endoscopic image processing system in accordance with the present invention will be described in conjunction with FIG. 19.

The electronic endoscopic system 201 comprises an endoscope system 202, an insertional shape-of-endoscope observing system 203, and an image processing system 204.

The endoscope system 202 comprises an electronic endoscope 212, a video processor 210, a light source unit 211, and an observation monitor 214.

The electronic endoscope 212 has an electronic image pickup device incorporated in the distal part of the elongated insertion unit that is inserted into the lumen of a body cavity, though the electronic image pickup device is not shown. The electronic image pickup device is driven or controlled in order to produce or transmit an image video signal representing a region to be observed in the lumen. The region to be observed in the lumen is illuminated using a light guide that lies through the insertion unit.

Furthermore, the distal part of the insertion unit of the electronic endoscope 212 has a bending section, and the bending section can be bent using an operating unit disposed at the proximal end of the insertion unit.

Furthermore, the operating unit of the electronic endoscope 212 has a Release switch 212*a*. A cable over which the electronic image pickup device is driven or controlled by the video processor 210 or a produced image video signal is transferred to or from the video processor 210, and a light guide cable that introduces illumination light, which is emitted from the light source unit 211, to a light guide are extended from the operating unit. When the Release switch 212*a* is handled, recording of a still image that will be described later is executed.

Moreover, the electronic endoscope 212 has a detecting facility for detecting the inserted position of the insertion unit in a lumen or the shape thereof, though the detecting facility is not shown. The insertional shape detecting facility comprises, similarly to the aforesaid conventional one, a plurality of source coils incorporated in the insertion unit of the endoscope and a plurality of sense coils incorporated in the insertional shape-of-endoscope observing system 203. The sense coils are not shown.

The video processor 210 drives or controls the electronic image pickup device incorporated in the electronic endoscope 212. Moreover, the video processor 210 performs predetermined signal processing on an image video signal that results from photoelectric conversion performed by the electronic image pickup device, and thus produces a luminance signal and a color signal (Y/C signals) or red, green, and blue signals (RGB signals).

The Y/C signals or RGB signals produced by the video processor 210 are directly transmitted to each of the observation monitor 214 and image processing system 215.

Moreover, when the Release switch 212a is handled, transmission of a still image of an image or a picture can be directed.

The video processor 210 has a facility for receiving examination information on endoscopic examination, though the facility is not shown.

The light source unit 211 includes a lamp serving as an illumination light source and a circuit for lighting the lamp. Illumination light projected with the lamp lit is fed to the light guide extending from the electronic endoscope 212, and irradiated to the region to be observed in a lumen through the distal end of the insertion unit.

On the observation monitor 214, an endoscopic image is displayed based on the Y/C signals or RGB signals produced by the video processor 210.

The insertional shape-of-endoscope observing system 203 is a peripheral device of the endoscope system 202. The insertional shape-of-endoscope observing system 203 includes a shape processing unit 213 and a monitor 213b. Based on a magnetic field induced by the source coils, which are incorporated in the electronic endoscope 212, and detected by the sense coils that are not shown and that are incorporated in the insertional shape-of-endoscope observing system 203, the shape processing unit 213 calculates coordinates representing the positions of the source coils. Moreover, the shape processing unit 213 infers the shape of the insertion unit from the calculated coordinates representing the positions, and produces a shape-of-insertion unit image signal. Based on the shape-of-insertion unit image signal produced by the shape processing unit 213, an insertional shape image is displayed on the monitor 213b.

The insertional shape-of-endoscope observing system 203 can modify an angle of rotation, by which a shape-of-insertion unit image produced by the shape processing unit 213 and displayed on the monitor 213b is rotated, an enlargement or reduction ratio of the image, and other attribute for presentation of a shape in response to a directive entered at an operator panel that is not shown.

The shape processing unit 213 has a communications port 213a through which insertional shape data specifying coordinates in a three-dimensional space, which indicate the insertional shape of the endoscope, and the attributes for presentation of the shape is transmitted to the image processing system 204.

Only insertional shape data produced when the Release switch 212a included in the electronic endoscope 212 is handled may be transmitted.

The image processing system 204 includes a personal computer 215 (hereinafter PC 215), a mouse 216 and a keyboard 217 to be used to enter various directions that are transmitted to the PC 215, and a display 218 on which various pieces of information treated by the PC 215 and image information are reproduced and presented.

Furthermore, the PC 215 has: a communications port 215a through which insertional shape data sent from the shape processing unit 213 included in the insertional shape-of-endoscope observing system 203 through the communications port 213a is received; a communications port 215b through which endoscopic examination information sent from the video processor 210 connected to the endoscope 2 through the communications port 210a is received; and a motion picture input port 215c through which a motion picture video signal produced by the video processor 210 connected to the endoscope 2 is converted into predetermined compressed image data.

In other words, a motion picture video signal produced by the video processor 210 is transferred to the image processing system 204 through the motion picture input port 215c. The motion picture video signal is converted into a predetermined compressed motion picture video signal, for example, compressed image data conformable to the MJPEG standard, and preserved in a recording device that is included in the PC 215 and that is not shown.

In general, prior to the start of endoscopic examination, examination information on endoscopic examination is received from the video processor 210. Based on the received examination information, characters or numerals are displayed on the observation monitor 214. Moreover, the examination information may be transmitted to the image processing system 204 through the communications ports 210a and 215b, and recorded therein.

Incidentally, what is referred to as examination information includes, for example, a patient name, a date of birth, a sex, an age, a patient code, and a date of examination.

The image processing system 204 is, if necessary, connected to the video processor 210. Various pieces of information are received from the video processor 210 and preserved in the image processing system 204.

Actions to be performed in the image processing system 204 included in the electronic endoscopic system 201 having the foregoing components will be described below. To begin with, a process of receiving and preserving insertional shape-of-endoscope data sent from the shape processing unit 213 included in the insertional shape-of-endoscope observing system 203 and examination information and an endoscopic image sent from the video processor 210 will be described in conjunction with FIG. 20 and FIG. 23.

The process is implemented in an endoscopic examination application installed in the image processing system 204. Prior to the start of endoscopic examination, the video processor 210 receives examination information, and the image processing system 204 invokes the endoscopic examination application. When the endoscopic examination application is invoked, an examination window 300 shown in FIG. 23(a) and an endoscopic image window 305 shown in FIG. 23(b) are opened on the display 218.

After the PC 215 included in the image processing system 204 invokes the endoscopic examination application and the examination window 300 is opened on the display 218, the PC 215 enters, at step S201, a mode in which examination information and endoscopic image data are received from the video processor 210 and preserved.

Thereafter, at step S202, the PC 215 judges whether an operator has turned on an examination start button (Start Exam. button in the drawing), which is displayed in the examination window 300, using the mouse 216 or keyboard 217. The PC 215 stands by until the examination start button 301 is turned on. When the examination start button 301 is turned on, processing started at step S203 is executed.

At step S203, the PC 215 starts communicating with the shape processing unit 213 included in the insertional shape-of-endoscope observing system 203 through the communications port 215a. At step S204, the PC 215 starts communicating with the video processor 210 through the communications port 215b.

At step S205, the PC 215 transmits an examination information acquisition command to the video processor 210 through the communications port 215b and the communications port 210a of the video processor 210. In response to the examination information acquisition command, the video processor 210 transmits examination information to the PC 215.

At step S206, the PC 215 records or preserves the examination information, which is sent from the video processor 210 at step S205, in the recording device that is not shown.

Thereafter, at step S207, the PC 215 transmits an insertional shape data acquisition command to the shape processing unit 213 through the communications port 215a and the communications port 213a of the shape processing unit 213. In response to the insertional shape data acquisition command, the shape processing unit 213 starts transmitting insertional shape data. This transmission continues until the communications port 215a is broken after the communication between the PC 215 and shape processing unit 213 is terminated.

At step S208, the PC 215 receives insertional shape data sent from the shape processing unit 213 at step S207. The PC 215 then records or preserves the insertional shape data in a hard disk, which is incorporated in the PC 215 and is not shown, in association with examination information recorded or preserved at step S206 (hereinafter, the insertional shape data may be referred to as an insertional shape file).

Thereafter, at step S209, the PC 215 converts a motion picture video signal, which is received from the video processor 210 via the motion picture input port 215c, into compressed image data conformable to the MJPEG standard. At step S206, the PC 215 records or preserves the compressed image data in the hard disk, which is incorporated in the PC 215 and is not shown, in association with the examination information recorded or preserved at step S206 (hereinafter, the compressed image data may be referred to as an image file). Moreover, the PC 215 displays a motion picture, which is received through the motion picture input port 215c, in an endoscopic image field 306 within the endoscopic image window 305 shown in FIG. 23(b).

Thereafter, at step S210, the PC 215 judges whether an examination end button 302 (End Exam. button in the drawing) within the examination window 300 has been clicked. If it is verified that the examination end button 302 has not been clicked, control is returned to step S208. If it is verified that the examination end button 302 has been clicked, the PC 215 terminates the communication of information between the shape processing unit 213 and video processor 210 through the communications ports 215a and 215b.

Thus, the image processing unit 204 receives the examination information that is sent from the video processor 210 included in the endoscope system 202, the endoscopic image data that is predetermined compressed image data into which a video signal produced by the electronic endoscope 212 is converted, and the insertional shape data produced by the insertional shape-of-endoscope observing system 203. Moreover, the image processing system 204 records or preserves the endoscopic image data and insertional shape data in the predetermined recording device in association with the examination information.

Thereafter, synchronous reproduction of an endoscopic image and an insertional shape image that is performed based on the examination information, endoscopic image data, and insertional shape data recorded or preserved in the image processing system 204 will be described in conjunction with FIG. 21 and FIG. 24.

In relation to the synchronous reproduction of an endoscopic image and an insertional shape image, suspension of reproduction, termination of reproduction, direct designation of a display frame, and modification of presentation attributes will be described below.

Incidentally, the presentation attributes include information on rotation of an insertional shape-of-endoscope image about an X-axis, and information on rotation thereof about a Y-axis. A system of coordinates defined in order to display an insertional shape image is presented through an insertional shape presentation screen 330 shown in FIG. 24(b). The presentation is implemented in a view application (hereinafter, called a viewer) installed in the image processing system 204. When the viewer is invoked, a reproduction control window 310 shown in FIG. 24(a), an insertional shape presentation window 330 shown in FIG. 24(b), and an endoscopic image window 335 shown in FIG. 24(c) are opened on the display 218.

The frame rates for an endoscopic image and an insertional shape image are determined, and a recording time instant at which the insertional shape image is preserved relative to each frame is recorded. Consequently, the synchronous reproduction of the endoscopic image and insertional shape image is achieved by creating a frame table in which a reproduction start time instant is adjusted in association with creation time instants at which an image file and an insertional shape file are created.

For example, assume that the creation time instant of an image file is 10:00:00, the creation time instant of an insertional shape file is 10:00:01, the frame rate for an endoscopic image is 30 frames per sec, and the frame rate for an insertional shape image is 15 frames per sec. A table of relationship between a frame number assigned to each endoscopic image frame contained in an image file and a frame number assigned to each insertional shape image frame contained in an insertional shape file is created similarly to table 1. The relationship table is referenced in order to display associated frames, whereby the synchronous reproduction is achieved.

In order to solely reproduce an endoscopic image or an insertional shape-of-endoscope image, the relationship listed in table 1 is not employed, but an interval between time instants at which a reproduction timer enables processing as described below is determined based on the frame rates.

TABLE 1

| Endoscopic image frame number | Insertional shape image frame number |
|---|---|
| 0 | No associated one |
| 1 | No associated one |
| ⋮ | ⋮ |
| 29 | No associated one |
| 30 | 1 |
| 31 | 1 |
| 32 | 2 |
| 33 | 2 |
| ⋮ | ⋮ |

First, for synchronous reproduction of an endoscopic image and an insertional shape image, an operator invokes the viewer residing in the PC 215. Consequently, the reproduction control window 310 shown in FIG. 24(a), the insertional shape presentation window 330 shown in FIG. 24(b), the endoscopic image window 335 shown in FIG. 24(c) are opened on the display 218.

When the reproduction control window 310 is opened, the PC 215 prompts an operator to designate an image file, which is needed to synchronously reproduce an endoscopic image and an insertional shape image, at step S221. For example, the mouse 216 or keyboard 217 is used to click a reproduction button (Play button in the drawing) 311 within the reproduction control window 310. Consequently, a file selection window is opened on the display 218. When an image file is designated through the file selection window, an insertional shape file associated with examination information recorded in the image file is selected as a partner in synchronous reproduction. The number of frames contained in the image file shall be Nf.

As mentioned above, when an operator designates an image file through the file selection window opened on the display 218, an insertional shape file associated with the image file is selected. At step S222, the PC 215 initializes the scale on a slide controller 314 within the reproduction control window 310 so that the minimum reading of the slide controller 314 will be 0 and the maximum reading thereof will be Nf–1.

Thereafter, at step S223, the PC 215 initializes various variables. In the initialization of various variables, a status St that signifies a current operating state is set to reproduction Playback, a display frame number Frm is set to 0, an angle of rotation about the X-axis θx is set to 0, and an angle of rotation about the Y-axis θy is set to 0.

Incidentally, the reproduction frame number Frm signifies a frame number of an endoscopic image. When an insertional shape image is displayed, an insertional shape frame number associated with the frame number Frm of the endoscopic image is retrieved from the table of relationship like table 1.

When the initialization of various variables of step S223 is completed, the PC 215 activates a reproduction timer at step S224. The timer is a software timer employed in software multiplexing or the like.

The reproduction timer enables display of an endoscopic image and display of an insertional shape image at regular intervals. The interval between time instants at which the timer enables processing is 1/f sec where f denotes the frame rate (fps) for an endoscopic image.

When activation of the timer of step S224 is completed, the PC 215 verifies at step S225 whether a reproduction end button (Stop button in the drawing) 313 in the reproduction control window 310 has been clicked. If it is verified that the reproduction end button 313 has been clicked, the reproduction timer is inactivated at step S236, and the synchronous reproduction and display of an endoscopic image and an insertional shape image is terminated. If it is verified that the reproduction end button 313 has not been clicked, it is verified at step S226 whether a lever 314a of the slide controller 314 in the reproduction control window 310 is moved.

The slide controller 314 that is checked at step S226 is used to directly designate a frame of an endoscopic image which the operator wants to reproduce. The designated endoscopic image and an associated insertional shape image can be displayed.

If the lever 314a of the slide controller 314 has been moved in order to designate a frame of an endoscope image that is to be reproduced, synchronous reproduction is suspended. If the lever 314a has been moved, processing started at step S227 is executed. If the lever 314a has not been moved, processing started at step S230 is executed.

If it is verified at step S226 that the lever 314a of the slide controller 314 has been moved in order to designate a frame of an endoscopic image to be reproduced and displayed, the PC 215 sets the status to suspension (St=Pause) so as to suspend update of an endoscopic image and an insertional shape image that is enabled by the reproduction timer.

Thereafter, at step S228, the PC 215 detects a reading of the slide controller 314 at the position of the lever 314a that has been moved. The PC 215 then sets the display frame number Frm, which indicates a frame in the endoscopic image file, to the reading at the position. At step S229, an endoscopic image frame that is identified with the display frame number Frm determined at step S228 and that is contained in the endoscopic image file is displayed in the image display screen 335 shown in FIG. 24(c). Moreover, insertional shape data associated with the frame number Frm and its presentation attributes are retrieved from an insertional shape file. An insertional shape image is rotated based on the presentation attributes including the angle of rotation about the X-axis θx and the angle of rotation about the Y-axis θy, and thus reconstructed. The reconstructed insertional shape image is displayed within the insertional shape presentation screen 330 shown in FIG. 24(b). Control is then returned to step S225.

Incidentally, the endoscopic image window 335 and insertional shape window 330 may be opened on the display 218 while being superimposed on each other. Otherwise, an endoscopic image and an insertional shape image may be reduced on an appropriate scale according to given settings so that the windows will not be superimposed on each other. A user may be permitted to modify the sizes of the windows.

If it is verified at step S226 that the lever 314a of the slide controller 314 has not been moved, the PC 215 verifies at step S230 whether a reproduction button (Play button in the drawing) 311 in the reproduction control window 310 has been clicked. If it is verified that the reproduction button 311 has not been clicked, processing started at step S232 is executed. If it is verified that the reproduction button 311 has been clicked, the PC 215 sets at step S231 the status to reproduction (St=Playback), and restarts update of an endoscopic image and an insertional shape image that is enabled by the reproduction timer. Control is then returned to step S225.

If it is verified at step S230 that the reproduction button 311 has not been clicked, the PC 215 verifies at step S232 whether the suspension button (Pause button in the drawing) 312 in the reproduction control window 310 has been clicked. If it is verified that the suspension button 312 has not been clicked, processing started at step S234 is executed. If it is verified that the suspension button 312 has been clicked, the PC 215 sets the status to suspension (St=Pause) at step S233, and thus suspends update of an endoscopic image and an insertional shape image that is enabled by the reproduction timer. Control is then returned to step S225.

If it is verified at step S232 that the suspension button 312 has not been clicked, the PC 215 verifies at step S234 whether an insertional shape image rotation button (upward, downward, rightward, and leftward arrow keys in the drawing) 315 has been clicked. If it is verified that the insertional shape image rotation button 315 has not been clicked, control is returned to step S225. If it is verified that the insertional shape image rotation button 315 has been clicked, an angle of rotation by which an insertional shape image is rotated is increased or decreased at step S235 based on the click in the insertional shape image rotation button 315. Control is then returned to step S225.

The angle of rotation is increased or decreased at step S235. At this time, if a rightward arrow (→) key included in the insertional shape image rotation button 315 is clicked, the angle of rotation about the Y-axis θy is increased by Cy. If a leftward arrow (←) key is clicked, the angle of rotation about the Y-axis θy is decreased by Cy. If an upward arrow (↑) key is clicked, the angle of rotation about the X-axis θx is decreased by Cx. If a downward arrow (↓) key is clicked, the angle of rotation about the X-axis θx is increased by Cx.

Incidentally, Cx and Cy denote given constants indicating a magnitude of increase or decrease in an angle of rotation by which an insertional shape image is rotated. The unit for Cx and Cy is radian that is a unit of angular measurement. By changing the constant Cx and Cy, a degree to which an insertional shape image is rotated can be varied with every click in the insertional shape image rotation button 315.

Next, the reproduction timer employed at step S224 will be described in conjunction with FIG. 22. The reproduction timer has the capability to enable display of an endoscopic image and an insertional shape image and the capability to enable update of the position of the lever 314a on the slide controller 314. owing to the capability to enable update of the position of the lever 314a, an operator can readily recognize which of all frames constituting an endoscopic image is being displayed.

Incidentally, the multithreading technique may be adopted for software multiplexing realized using the software timer.

When the reproduction timer is called at intervals of 1/f sec, the PC 215 verifies at step S241 whether the status is set to reproduction (St=Playback). If it is verified that the status is not set to reproduction, the reproduction timer is terminated. If the status is set to reproduction, control is passed to step S242.

At step S242, the PC 215 decodes data that represents an endoscopic image frame designated to be displayed and that is contained in the endoscopic image file. The PC 215 then displays an image in the endoscopic image display field 336 within the endoscopic image display screen 335 according to the decoded data.

Thereafter, at step S243, the PC 215 reads insertional shape data and presentation attributes, which are associated with an endoscopic image frame that is displayed in the endoscopic image display field 336 at step S242, from an insertional shape file. An insertional shape image is reconstructed or rotated based on the presentation attributes including the angle of rotation about the X-axis θx and the angle of rotation about the Y-axis θy, and displayed in the insertional shape image display field 331 within the insertional shape display window 330. The rotations of the insertional shape image about the X-axis and Y-axis are achieved by performing the known coordinate transformation on coordinates in the three-dimensional space that represent points on the insertional shape image.

Thereafter, the PC 215 increments the display frame number Frm by 1 (Frm+1) at step S244, and judges at step S245 whether the display frame number Frm is set to Nf−1. Namely, it is verified whether all the frames ending with the last one have been reproduced and displayed.

If it is verified at step S245 that all the frames ending with the last one have been reproduced and displayed, the PC 215 inactivates the timer at step S246.

If it is verified at step S245 that all the frames ending with the last one have not been reproduced and displayed, the PC 215 moves the lever 314a of the slide controller 314 to the position of a reading corresponding to a frame number that results from the increment of the display frame number Frm by one performed at step S244. The reproduction timer is then terminated.

Consequently, endoscopic image data and insertional shape data recorded or preserved in the image processing system 204 can be used and synchronously reproduced in order to display an endoscopic image and an insertional shape image on the display 218.

Incidentally, the facilities constituting the image processing system 204 may be incorporated in the video processor 210 or insertional shape-of-endoscope observing system 203.

Moreover, the form in which an endoscopic image is preserved is not limited to the form of a motion picture. Still images may be preserved successively as long as their recording time instants are clearly recorded. Even in this case, the same advantage as the aforesaid one can be provided.

As mentioned above, when endoscopic image data and insertional shape data are recorded or preserved and synchronously reproduced, the endoscopic image and the shape of the endoscope insertion unit attained during formation of the image can be freely collated with each other. This will prove helpful in training of insertion or handling of an endoscope.

Moreover, after endoscopic examination is completed, synchronous reproduction is performed with the attributes for presentation of the shape of an endoscope insertion unit varied. This will prove helpful in exploring the cause of the difficulty in inserting an endoscope or the cause of patient discomfort.

Figure 26:
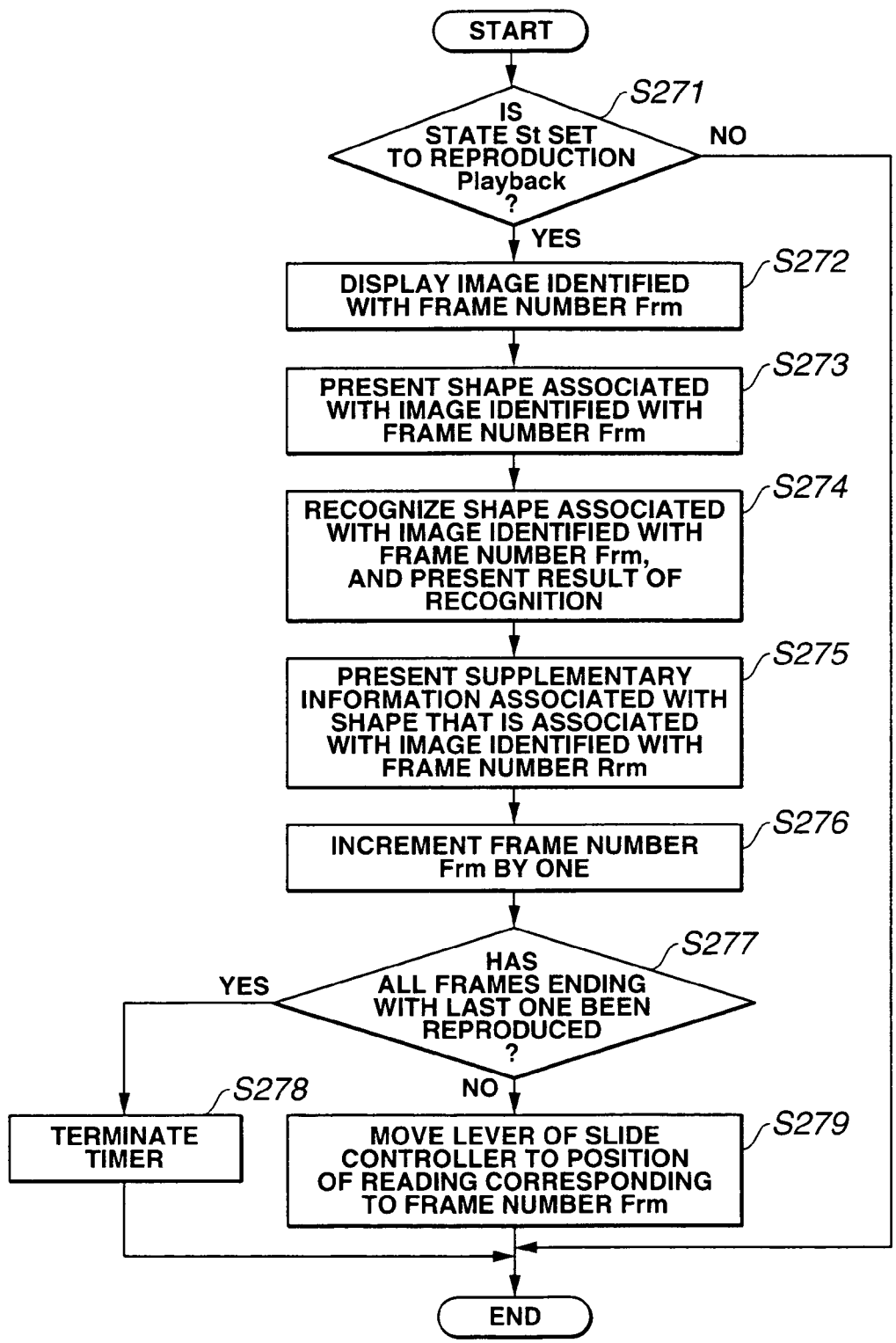
FIG. 26 is a flowchart describing the action of a reproduction timer enabling synchronous reproduction of an endoscopic image, an insertional shape-of-endoscope image, and supplementary information that is executed in the electronic endoscopic system employing the seventh embodiment of the present invention.
Figure 27:
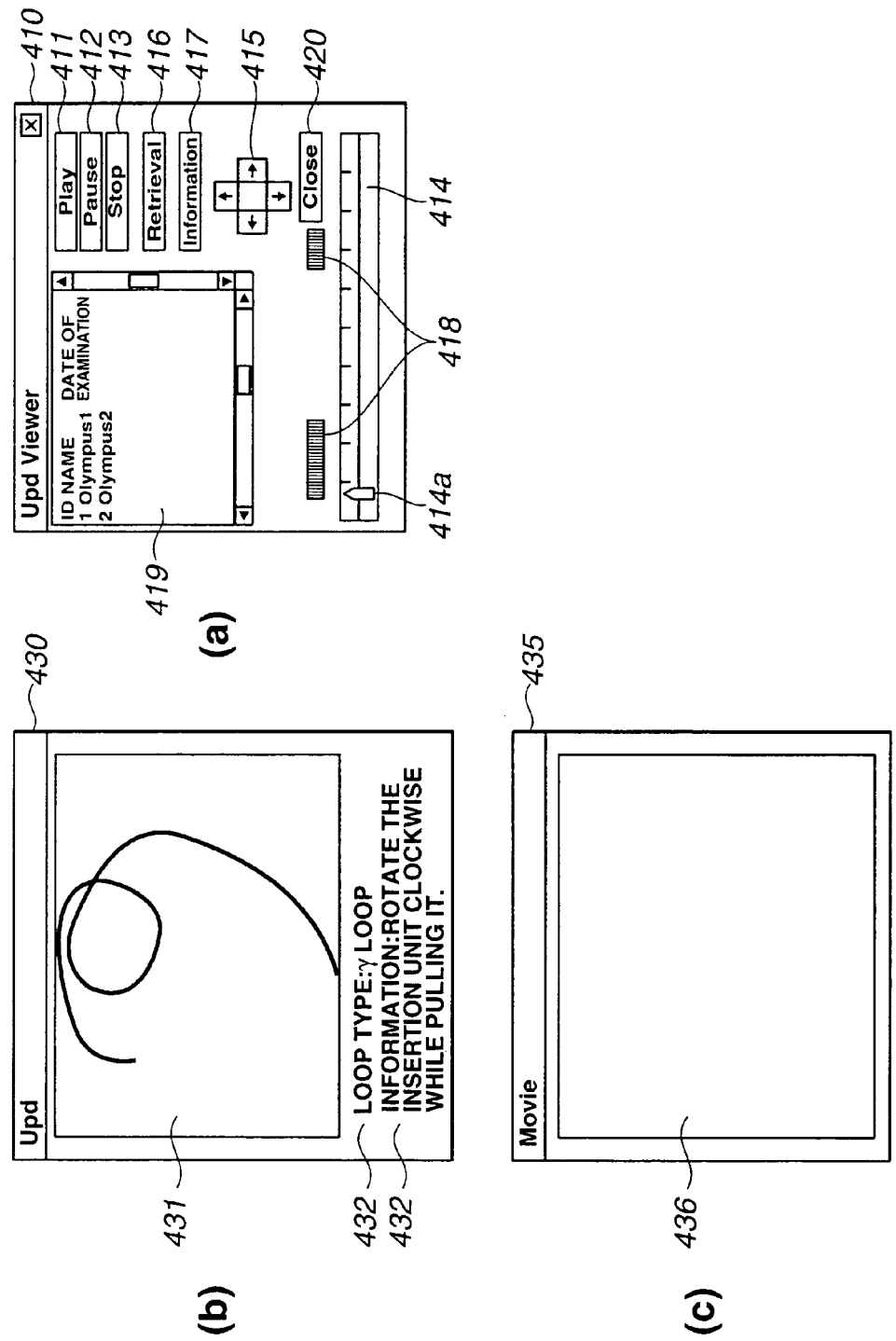
FIG. 27 shows display screen images displayed during synchronous reproduction of an endoscopic image, an insertional shape-of-endoscope image, and supplementary information that is executed in an electronic endoscopic system employing the seventh embodiment of the present invention.

Next, a seventh embodiment of an image processing system in accordance with the present invention will be described in conjunction with FIG. 25 to FIG. 27. The seventh embodiment includes a facility that retrieves a desired endoscopic image and desired insertional shape-of-endoscope image from endoscopic examination information, endoscopic image data, and insertional shape data which are recorded or preserved during endoscopic examination, and appends information to the retrieved endoscopic image and insertional shape-of-endoscope image.

In order to implement the retrieving and information appending facility included in the seventh embodiment, The PC 215 invokes a viewer that is the retrieving and information appending facility. The viewer opens on the display 218 a reproduction control window 410 for retrieval and information appending shown in FIG. 27(a), an insertional shape window 430 shown in FIG. 27(b), and an endoscopic image window 435 shown in FIG. 27(c).

The retrieving and information appending facility will be described by taking retrieval of the looped shape of the endoscope insertion unit for instance. Incidentally, an α loop, an N loop, and a γ loop are defined as recognizable loops in advance, and an insertional shape is considered to be a curve. Therefore, a technology for extracting the feature of a curve is employed. Herein, for brevity's sake, an insertional shape is considered to be a quadratic curve and characterized with, for example, a P-type Fourier descriptor. For the P-type Fourier descriptor, refer to the journal published by the Institute of Electronics, Information and Communication Engineers (Vol. j67-A, No. 3).

According to a technique employed in the present embodiment, first, a curve is divided into n segments (where n denotes a positive number indicating a divisor), and the limits of the segments are represented with complex numbers. A function of a total curvature at each limit is defined, and Fourier-transformed to produce a power spectrum. The power spectrum is considered to represent the feature of the curve. P-type Fourier descriptors characterizing loops are stored in advance. A power spectrum Cri(k) (where k denotes 0, etc., or n−1) represents the feature of each loop. Herein, i=0 signifies an α loop, i=2 signifies an N loop, and i=3 signifies a γ loop.

The actions to be performed by the retrieving and information appending facility will be described in conjunction with FIG. 25. At step S251, the PC 215 verifies whether examination information to be reproduced and displayed or to be retrieved has been selected through the reproduction control window 410 on the display 218.

Pieces of examination information to be reproduced and displayed or to be retrieved are presented through an examination information presentation field 419 within the reproduction control window 410. Desired examination information is selected from the examination information list using the mouse 216 or keyboard 217.

If it is verified at step S251 that examination information to be reproduced and displayed or to be retrieved has been selected from the endoscopic examination information list, the PC 215 highlights at step S252 the examination information that is selected from the examination information list presented through the examination information presentation field 419 within the reproduction control window 410.

If no examination information is selected from the endoscopic examination information list at step S251, examination information specified first in the examination information list is regarded to have been selected. The number of frames recorded in an image file associated with the selected examination information shall be Nf.

Thereafter, at step S253, the PC 215 verifies whether a retrieval button (Retrieval button in the drawing) 416 in the reproduction control window 410 has been clicked. If it is verified that the retrieval button 416 has not been clicked, processing started at step S260 is executed. If it is verified that the retrieval button 416 has been clicked, the status is set to retrieval (St=Retrieval) at step S254. Moreover, the display frame number Frm is set to 0, the angle of rotation about the X-axis θx is set to 0, and the angle of rotation about the Y-axis θy is set to 0. Incidentally, rotation about an axis is identical to that employed in the sixth embodiment.

Thereafter, at step S255, the PC 215 opens a retrieval information window, which is not shown, on the display 218. Retrieval information such as a loop shape to be retrieved is entered through the retrieval information window. Herein, information required to retrieve an α loop shall be entered.

If information on the α loop is entered as a looped shape to be retrieved at step S255, feature data is calculated based on insertional shape data relevant to each frame at step S256. The calculated feature data shall be a power spectrum $Cj(k)$ (where k denotes 0, etc., or n−1, and j denotes 0, etc., or Nf−1).

Thereafter, at step S257, the PC 215 calculates a distance between a value of the power spectrum $Cri(k)$, which represents the feature of a typical loop and is stored in advance, and a value of the power spectrum $Cj(k)$ calculated at step S256. For example, if the distance between the value of the power spectrum $Cri(k)$ representing the feature of the α loop and the value of the calculated power spectrum $Cj(k)$ is smaller than a threshold, the power spectrum $Cj(k)$ is judged to represent the feature of the α loop. The distance between the values of two power spectra relative to the same frequency is expressed with, for example, an euclidean distance. Thus, similarity between stored and calculated power spectra is verified relative to all frames.

At step 258, the PC 215 initializes the scale of the slide controller 414 so that the minimum reading will be 0 and the maximum reading will be Nf−1. At step S259, a graphic 218 indicating the readings that correspond to frame numbers associated with insertional shape data items which represent insertional shapes judged at step S256 and S257 to have similarity to stored looped shapes is displayed near the slid controller 414. The frame identification graphic 418 is displayed above the slide controller 141 within the reproduction control window 410 shown in FIG. 27(a). The frame identification graphic 418 may be painted in a color that varies depending on the type of loop.

Thereafter, at step S260, the PC 215 verifies whether the lever 414a of the slide controller 414 has been moved. If it is verified that the lever has not been mode, processing stared at step S263 is executed. If it is verified that the lever 414a has been moved, the position of the moved lever 414a is detected at step S261. The reproduction frame number Frm is set to a value corresponding to the reading at the position of the lever 414a. At step S262, an endoscopic still image frame of the specified frame number and an associated insertional shape-of-endoscope image are displayed. The way of display is identical to that at step S229.

The way of displaying an endoscopic still image and an insertional shape-of-endoscope image at step S262 is identical to that employed in the sixth embodiment. Specifically, the endoscopic image window 435 and insertional shape window 430 are appropriately superimposed on each other and displayed on the display 218. Otherwise, an endoscopic image and an insertional shape image are reduced on an appropriate scale according to given settings for fear both the windows may overlap.

Thereafter, at step S263, the PC 215 verifies whether an information entry button (Information button in the drawing) 417 in the reproduction control window 410 has been clicked. If it is verified that the information entry button has not been clicked, processing started at step S265 is executed. If it is verified that the information entry button 417 has been clicked, information to be appended to the endoscopic still image and insertional shape-of-endoscope image displayed on the display 218 is entered through an information entry window that is not shown. The entered supplementary information is recorded or preserved in association with the endoscopic examination information and reproduction frame number (Frm).

The supplementary information may be stored independently of the endoscopic image and insertional shape-of-endoscope image.

Thereafter, at step S265, the PC 215 verifies whether a reproduction button (Play button) 411 has been clicked. If it is verified that the reproduction button has been clicked, control is passed to synchronous reproduction started at step S222 (see FIG. 21). According to the seventh embodiment, synchronous reproduction started at step S222 and ended at step S236 is executed with the reproduction end button, reproduction button, suspension button, rotation button, and slide controller shown in FIG. 24 replaced with those shown in FIG. 27. After step S236 is executed, control shall be returned to step S251.

If it is verified that the reproduction button 411 has not been clicked, it is verified whether an end button (Close button in the drawing) 420 has been clicked. If it is verified that the end button 420 has not been clicked, control is returned to step S251. If it is verified that the end button 420 has been clicked, the viewer that is the retrieving and information appending facility is terminated at step S267.

As described above, after endoscopic examination is completed, supplementary information can be appended to an endoscopic image and an insertional shape-of-endoscope image that are retrieved under specific conditions for retrieval.

Synchronous reproduction of an endoscopic image and an insertional shape-of-endoscope image to which supplementary information is appended by the retrieving and information appending facility is basically identical to the processing from step S222 to step S236 described in FIG. 21. However, the action of the reproduction timer performed at step S224 is different. The action of the reproduction timer included in the retrieving and information appending facility will be described in conjunction with FIG. 26.

The reproduction timer included in the retrieving and information appending facility enables display of an endoscopic image frame and an insertional shape-of-endoscope image, presentation of supplementary information, and update of the position of the lever of the slide controller.

At step S271, the PC 215 verifies whether the status is set to reproduction (St=Playback). If it is verified that the status is not set to reproduction (Playback), the reproduction timer is terminated. If it is verified that the status is set to reproduction, a designated endoscopic image frame contained in an endoscopic image file is decoded at step S272. The decoded endoscopic image frame is displayed in the endoscopic image field 436 within the endoscopic image window 435, which is shown in FIG. 27(c), on the display 218.

Thereafter, at step S273, the PC 215 acquires insertional shape-of-endoscope data associated with the endoscopic image frame decoded at step S272, and the attributes for presentation of the data. The PC 215 then displays an insertional shape image, which is reconstructed or rotated based on the presentation attributes including the angle of rotation about the X-axis θx, and the angle of rotation about the Y-axis θy, in the insertional shape presentation field 431 within the insertional shape presentation window 430, which is shown in FIG. 27(b), on the display 218.

Figure 25:
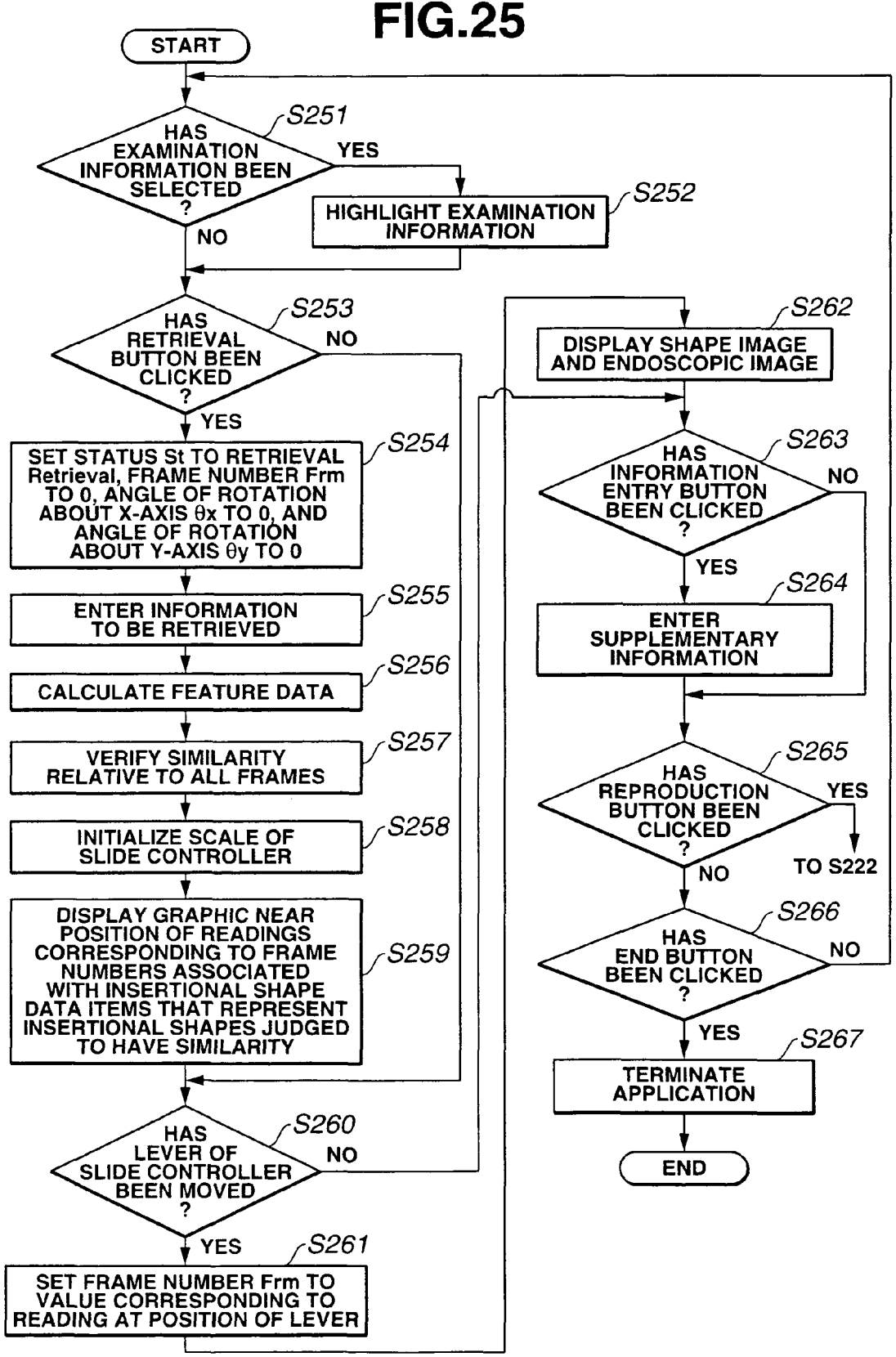
FIG. 25 is a flowchart describing appending of supplementary information to an endoscopic image and an insertional shape-of-endoscope image that is executed in an electronic endoscopic system employing a seventh embodiment of the present invention.

Furthermore, at step S274 similarly to at step S273, the PC 215 recognizes an insertional shape using insertional shape-of-endoscope data, which is associated with the decoded endoscopic image frame, in the same manner as it does at step S256 and step S257 (see FIG. 25). The PC 215 then displays the result of the recognition in a result-of-recognition presentation field 432 in the insertional shape presentation screen 430. The shapes the PC 215 can recognize include, for example, the α loop, N loop, and γ loop.

Thereafter, at step S275, the PC 215 retrieves supplementary information associated with the decoded endoscopic image frame, and presents the information in an information presentation field 433 within the insertional shape presentation window 430.

Thus, a designated endoscopic image frame, an associated insertional shape-of-endoscope image, the result of recognition, and supplementary information are displayed or presented on the display 218. At step S276, the PC 215 increments the reproduction frame number Frm, which indicates a frame being displayed on the display 218, by one (Frm+1). At step S277, the PC 215 verifies whether all frames ending with the last frame have been reproduced and displayed. If it is verified that all the frames ending with the last frame have been reproduced and displayed, the timer is terminated at step S278.

If it is verified at step S277 that all the frames ending with the last frame have not yet been reproduced and displayed, the lever 414a of the slide controller 414 is moved to the position of a reading corresponding to a frame number. The reproduction timer is then terminated.

As described above, according to the seventh embodiment, a desired image can be retrieved from among endoscopic images or insertional shape-of-endoscope images, which are produced during endoscopic examination, according to retrieval terms, and reproduced and displayed. Moreover, supplementary information can be entered and appended to the image that is retrieved, reproduced, and displayed.

The seventh embodiment has been described on the assumption that an insertional shape-of-endoscope image is retrieved and supplementary information is appended to the insertional shape-of-endoscope image. Apparently, endoscopic examination information may be retrieved and supplementary information may be appended to the endoscopic examination information. An endoscopic image may be retrieved and supplementary information may be appended to the endoscopic image.

The facilities constituting the image processing system 204 in accordance with the seventh embodiment may be incorporated in the video processor 210 or insertional shape-of-endoscope observing system 203.

Moreover, the form in which an endoscopic image is preserved is not limited to the form of a motion picture. Alternatively, still images may be successively preserved as long as their recording time instants are clearly recorded.

As mentioned above, supplementary information relevant to an endoscopic image and an insertional shape image is entered, recorded or preserved, and reproduced synchronously with the images. Consequently, an endoscopic image, the shape of an endoscope insertion unit attained during formation of the endoscopic image, and relevant information can be freely collated with one another. This will prove helpful in training of insertion or handling of an endoscope. In particular, when relevant information is entered, the preserved data can be used as an application aiding in self-study of insertion of an endoscope.

Moreover, after endoscopic examination is completed, while the attributes for presentation of the shape of an endoscope insertion unit are being varied, the shape image is reproduced synchronously with an endoscopic image. This will prove helpful in examining the cause of the difficulty in inserting an endoscope or the cause of patient discomfort. During the examination, relevant information can be appended. Thus, the results of discussion can be recorded or preserved.

Figure 28:
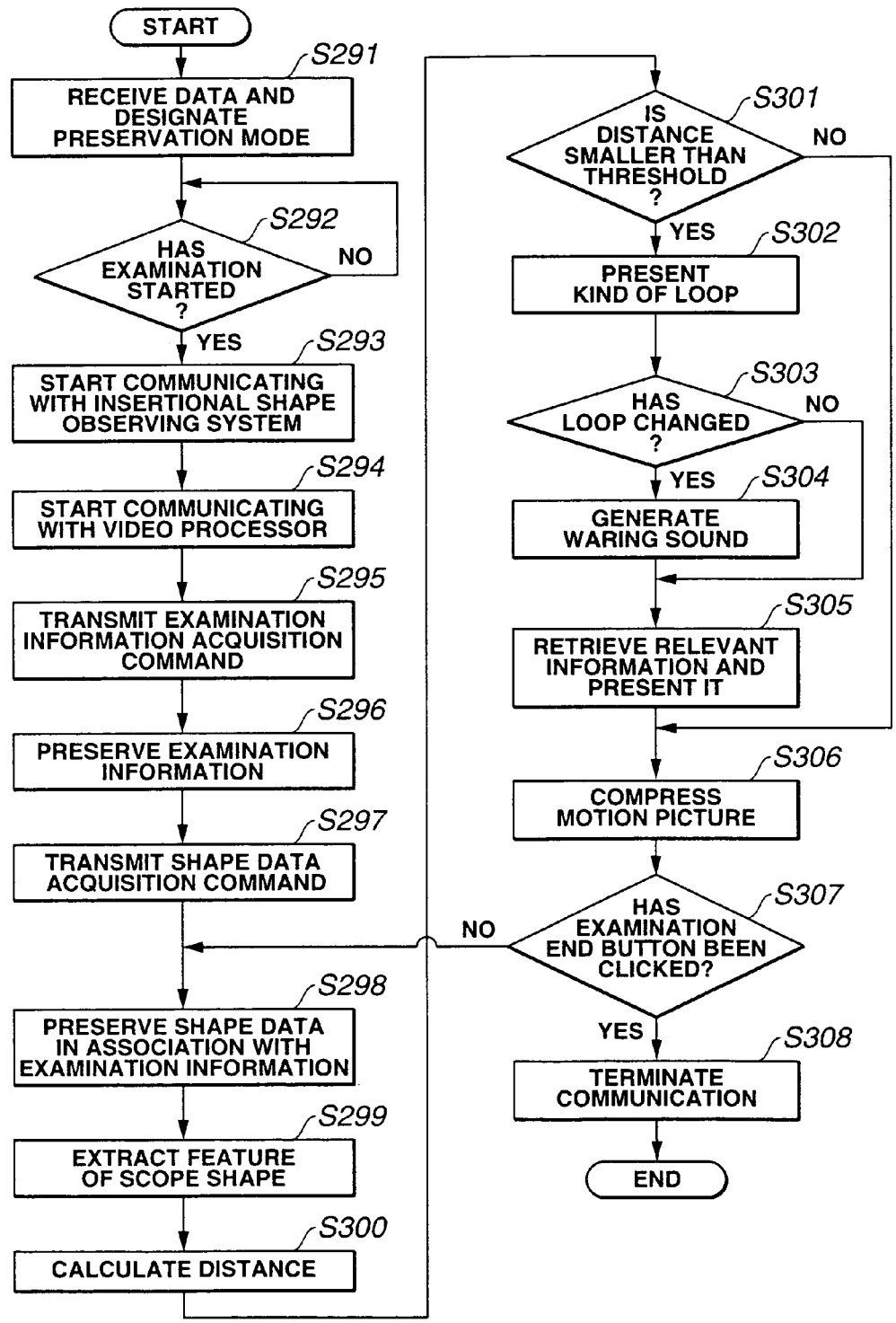
FIG. 28 is a flowchart describing search for a feature of an endoscopic image or an insertional shape-of-endoscope image, and display of information relevant to the feature that are executed in an electronic endoscopic system employing an eighth embodiment of the present invention.

Next, an eighth embodiment of the present invention will be described in conjunction with FIG. 28 and FIG. 29.

For example, when a colonoscope is used for endoscopic examination, while the endoscope insertion unit is being inserted into the large intestine, the insertion unit may be looped. The loop is called an α loop, an N loop, or a γ loop according to the shape.

When the loop is formed, it may cause a patient or a subject discomfort. Therefore, the looped endoscope insertion unit is restored to its original state or straightened in order to dissolve the patient discomfort.

A way of handling for straightening an endoscope insertion unit depends on a looped state. Therefore, the looped state of the insertion unit is recognized and presented, and the way of handling the endoscope insertion unit is presented, whereby the time required for endoscopic examination is shortened and patient discomfort is alleviated.

The eighth embodiment includes, in addition to the same facilities as those of the sixth embodiment, an insertional shape recognizing facility and a facility for presenting the result of the recognition and relevant information. These facilities are implemented in an examination application that is run in the image processing system 204.

Before endoscopic examination is started, the video processor 210 receives examination information, and the image processing system 204 invokes the examination application.

When the examination application is invoked, an examination window 500 shown in FIG. 29(a) and an endoscopic image window 505 shown in FIG. 29(b) are opened on the display 218.

The examination application will be described by taking an example. Within the example of examination application, the kind of loop formed by an endoscope insertion unit is recognized, the result of the recognition is presented, and a way of handling the endoscope insertion unit is retrieved based on the result of the recognition, and presented as relevant information.

Hereinafter, the kind of loop to be recognized shall include an α loop, an N loop, and a γ loop. Similarly to the seventh embodiment, P-type Fourier descriptors characterizing the kinds of loops shall be stored in advance. A power spectrum Cri(k) (where k denotes 0, etc., or n−1) shall represent the feature of each loop. Herein, i=0 signifies the α loop, i=2 signifies the N loop, and i=3 signifies the γ loop.

Ways of handling the endoscope insertion unit associated with respective looped states are registered in a database in advance. Using the result of recognition as a retrieval key, a way of handling the endoscope insertion unit can be retrieved.

As mentioned previously, when the examination application is invoked, the examination window shown in FIG. 29(a) and the endoscopic image window 505 shown in FIG. 29(b) are opened on the display 218. At step S291, the PC 215 enters a reception/preservation mode in which an endoscopic image received from the video processor 210 and an insertional shape-of-endoscope image received from the shape processing unit 213 are received and preserved. At step S292, the PC 215 stands by until an examination start button (Start Exam. button in the drawing) 501 in the examination window 500 is clicked using the mouse 216 or keyboard 217.

When the examination start button 501 is clicked, the PC 215 starts communicating with the shape processing unit 213 included in the insertional shape-of-endoscope observing system 203 through the communications port 215a.

Thereafter, at step S294, the PC 215 starts communicating with the video processor 210 through the communications port 215b. At step S295, an examination information acquisition command is transmitted to the video processor 210 through the communications port 215b and the communications port 210a of the video processor 210. The video processor 210 having received the examination information acquisition command through the communications port 210a transmits endoscopic examination information to the PC 215 by reversing a path along which the examination information acquisition command is transmitted.

At step S296, the PC 215 receives endoscopic examination information sent from the video processor 210 at step S295, and records or preserves the information in a recording memory that is not shown.

Thereafter, at step S297, the PC 215 transmits an insertional shape-of-endoscope data acquisition command to the shape processing unit 213 through the communications port 215a and the communications port 213a of the shape processing unit 213. The shape processing unit 213 having received the insertional shape data acquisition command through the communications port 213a starts transmitting insertional shape-of-endoscope data to the PC 215 by reversing the path along which the insertional shape-of-endoscope data acquisition command is transmitted.

At step S298, the PC 215 receives the insertional shape-of-endoscope data sent from the shape processing unit 213 at step S297. The PC 215 then records or preserves the insertional shape-of-endoscope data in association with endoscopic examination information, which is recorded or preserved at step S296, in the hard disk thereof that is not shown.

Thereafter, at step S299, the PC 215 extracts the feature of an insertional shape from the received insertional shape data. For the extraction of the feature of an insertional shape, a P-type Fourier descriptor is calculated (in the same manner as it is at step S256 described in FIG. 25 and employed in the seventh embodiment). A power spectrum C(k) (where k denotes 0, etc., or n−1, and n denotes a positive number serving as a divisor by which a curve is divided) shall be derived from the Fourier descriptor.

If the feature of the insertional shape is extracted at step S299, the PC 215 calculates at step S300 a distance between a value of the power spectrum C(k) relative to a certain frequency and a value of the power spectrum Cri(k) relative to the same frequency. The distance is, for example, an euclidean distance.

The distance calculated at step S300 is compared with a predefined threshold at step S301.

If the result of the comparison at step S300 demonstrates that the distance calculated at step S300 is larger than the threshold, processing started at step S306 is executed. If it is verified that the distance is smaller than the threshold, processing started at step S302 is executed.

If it is verified that the distance calculated at step S301 is smaller than the threshold, the PC 215 presents through the display 218 the result of recognition, which is performed on the kind of loop formed by the endoscope insertion unit, at step S302. The result of recognizing the kind of loop is presented through a result-of-recognition presenter section 503 of the examination window 500 (loop name or the like).

Thereafter, at step S303, the PC 215 verifies whether the looped shape of the insertion unit has changed. If it is verified that the looped shape has changed, a warning sound is generated at step S304. The generation of the warning sound prompts an operator to view an insertional shape-of-endoscope image displayed on the monitor 213b of the insertional shape-of-endoscope observing system 203.

If it is verified at step S303 that the looped shape of the insertion unit has not changed, or if a warning sound is generated at step S304, the PC 215 retrieves at step S305 relevant information on the basis of the result of recognizing the looped shape of the endoscope insertion unit. The retrieved relevant information is presented through a relevant information presenter section 504 of the examination window 500 opened on the display 218.

In other words, information on a way of handling the endoscope insertion unit according to a looped state that is one of the ways of handling recorded or preserved in the database in advance is presented through the relevant information presenter section 504. An operator can proceed with handling of the endoscope with reference to the presentation.

Thereafter, at step S306, the PC 215 converts a motion picture video signal, which is received from the video processor 210 through the motion picture input port 215c, into compressed image data conformable to the MJPEG standard. The PC 215 then records or preserves the compressed image data in association with the endoscopic examination information in a file in the hard disk thereof that is not shown. The image received from the video processor 210 is displayed in the image display field 506 of the display 218 in which an endoscopic image 505 is displayed.

Thereafter, at step S307, the PC 215 verifies whether an examination end button (End Exam. button in the drawing) 502 in the examination window 500 has been clicked. If it is verified that the examination end button has not been clicked, control is returned to the step S298. If it is verified that the examination end button 502 has been clicked, the PC 215 terminates at step S308 the examination application by breaking the communications ports 215a and 215b through which the shape processing unit 213 communicates with the video processor 210.

The eighth embodiment has been described in relation mainly to an insertional shape of an endoscope. The eighth embodiment can be applied to endoscopic examination information or an endoscopic motion picture.

Moreover, the eighth embodiment has been described as the image processing system 204. The same facilities as those of the image processing system 204 may be incorporated in the video processor 210 or insertional shape-of-endoscope observing system 203.

Furthermore, the form in which an endoscopic image is preserved is not limited to the form of a motion picture. Still images may be successively preserved as long as the recording time instants can be accurately recorded.

As mentioned above, the looped shape of an endoscope insertion unit is recognized, the recognized looped state is presented, and a way of handling the endoscope or any other relevant information is presented. This helps an operator accurately grasp the insertional shape of the endoscope, prompts the operator to review the relevant information. Eventually, the time required for endoscopic examination can be shortened, and patient discomfort can be alleviated.

The present invention is not limited to the aforesaid embodiments. Needless to say, various modifications and applications can be made within the scope of the invention without a departure from the gist thereof.

Industrial Applicability

As described so far, according to the present invention, when the insertional shape of an endoscope insertion unit is analyzed, information helpful in improving the ease of insertion of the endoscope can be provided. Consequently, the time required for endoscopic examination can be shortened, and patient discomfort can be alleviated.

Moreover, according to the present invention, an endoscopic image and an insertional shape-of-endoscope image can be synchronously reproduced based on endoscopic image data and insertional shape-of-endoscope data that are recorded or preserved. The endoscopic image and insertional shape-of-endoscope image can be freely collated with each other.

Moreover, after endoscopic examination is completed, synchronous reproduction is performed with the attributes for presentation of the insertional shape being varied. Thus, while actual endoscopic examination is being reproduced, training can be given for insertion or handling of an endoscope. Moreover, the cause of difficulty in inserting an endoscope during endoscopic examination or the cause of patient discomfort can be examined. Moreover, the present invention will prove useful for practice in handling of an endoscope system.

CROSS-REFERENCE FOR RELATED APPLICATIONS

The present applications claims a priority from Japanese Patent Application No. 2002-314699 filed in Japan on Oct. 29, 2002 and Japanese Patent Application No. 2003-162844 filed in Japan on Jun. 6, 2003. The contents of the disclosures are cited in the specification of the present application, Claims, and the drawings alike.

The invention claimed is:

1. An endoscopic information processing system comprising:
a shape analyzing unit for analyzing an insertional shape acquired by detecting the shape of an insertion unit of an endoscope which is inserted into a body cavity, the analyzing performed by the shape analyzing unit including:
detecting a looped portion along the insertion unit,
calculating a direction of rotation and a size of a looped portion where a loop is formed by an insertion operation of the insertion unit,
calculating a direction of a plane on which the detected looped portion is formed, and
determining whether a distal part of the insertion unit is located closer to or farther from a viewing point relative to the plane on which the looped portion is formed, the viewing point being a position or angle from which the representation of the endoscope is being viewed on a display; and
an information providing unit for providing an operating method for bringing the insertion unit from a current situation into a situation in which a loop of the looped portion is canceled based on the analysis performed by the shape analyzing unit, the operating method being a series of steps for manipulating the endoscope to be carried out in succession provided in graphical, written, and/or audio form, the information providing unit using the analysis performed by the shape analyzing unit to determine the operating method in order to cancel a looped state of the insertion unit by straightening the insertion unit.

2. An endoscopic information processing system according to claim 1, further comprising a shape storage unit for storing a plurality of insertional shapes acquired by detecting the shape of the insertion unit of the endoscope that is inserted into a body cavity, wherein:
the shape analyzing unit analyzes the shape of the endoscope insertion unit on the basis of the plurality of shapes of the endoscope insertion unit stored in the shape storage unit.

3. An endoscopic information processing system according to claim 1, wherein the information providing unit provides information on the shape of the endoscope insertion unit according to the analysis performed by the shape analyzing unit.

4. An endoscopic information processing system according to claim 1, wherein the information providing unit presents the operating method on a display device.

5. An endoscopic information processing system according to claim 1, wherein the information providing unit presents the operating method by means of a sound or voice.

6. An endoscopic information processing system according to claim 1, further comprising:
a shape detecting unit including a plurality of magnetic field generating members that generates a magnetic field, and a plurality of magnetic field detecting members that detects the magnetic field generated by the magnetic field generating members, and having either of the plurality of magnetic field generating members and the plurality of magnetic field detecting members disposed in the insertion unit; and
a shape inferring unit that infers the shape of the insertion unit based on the detection performed by the shape detecting unit.

7. An endoscopic information processing system according to claim 1, further comprising a shape inferring unit having a plurality of detecting members, which detects a physical property of a specific part of the insertion unit, disposed in the insertion unit, the shape inferring unit inferring the shape of the insertion unit based on the result of detecting the physical quantity and positions at which the detecting members are located.

8. An endoscopic information processing system according to claim 7, wherein the detecting members are a plurality of sensors that detects a deformation as the physical property.

9. An endoscopic information processing system according to claim 7, wherein the detecting members are a plurality of sensors that detects a displacement as the physical property.

10. An endoscopic information processing system according to claim 1, wherein the shape analyzing unit includes a calculating block that calculates a magnitude of a movement made by a specific part of the insertion unit, and an inferring block that infers a state of the insertion unit from the magnitude of the movement made by the specific part of the insertion unit.

11. An endoscopic information processing system according to claim 1, wherein the information providing unit presents, through a display device, information on the result of the analysis performed by the shape analyzing unit.

12. An endoscopic information processing system according to claim 11, wherein information presented through the display device is provided in the form of characters and/or a graphic.

13. An endoscopic information processing system according to claim 1, wherein the information providing unit presents information on the result of the analysis performed by the shape analyzing unit by means of a sound or voice.

14. An endoscopic information processing system according to claim 1, further comprising:
   a first data preserving unit that preserves first data that is the operating method provided by the information providing unit;
   a second data preserving unit that receives second data, which is examination information containing an endoscopic image, from an endoscope system, and preserves the data in association with the first data; and
   a reproducing unit that presents through a monitor the data, which are preserved in the first and second data preserving units, synchronously with each other or independently of each other.

15. An endoscopic information processing system according to claim 14, further comprising:
   a retrieval executing unit for executing retrieval of data according to features exhibited by the first and second data; and
   a result-of-retrieval information appending unit for appending relevant information to data retrieved by the retrieval executing unit, wherein:
   the reproducing unit presents information, which is appended by the result-of-retrieval information appending unit, through a monitor during reproduction of the first and second data items.

16. An endoscopic information processing system according to claim 14, further comprising:
   a data analyzing unit for analyzing the first data and/or the second data that are preserved in the first data preserving unit or second data preserving unit; and
   a processing unit that determines and executes processing according to the result of the analysis performed by the data analyzing unit.

17. An endoscopic information processing system according to claim 14, wherein the reproducing unit reads the operating method from the first data preserving unit, reads endoscopic image data from the second data preserving unit, and presents an endoscopic image, which is represented by the read endoscopic image data, and the operating method which is associated with the endoscopic image data, through the monitor according to information on an acquisition time instant at which the operating method is acquired and information on an acquisition time instant at which the endoscopic image data is acquired.

18. An endoscopic information processing system according to claim 17, wherein the operating method includes insertional shape data concerning the endoscope insertion unit.

19. An endoscopic information processing system according to claim 18, further comprising:
   a relevant information input unit for use in entering supplementary information relevant to the endoscopic image displayed on the monitor by the reproducing unit or relevant to the insertional shape presented through the monitor thereby; and
   a supplementary information storage unit in which supplementary information entered at the relevant information input unit is stored in association with the endoscopic image or insertional shape.

20. The endoscopic information processing system according to claim 1, wherein the information providing unit provides one method determined among straightening operation methods in graphical, written, and/or audio form, the straightening operation methods including:
   rotating the endoscope clockwise when the distal part is located away from the viewing point in a case where the direction of rotation of the looped portion is counterclockwise;
   rotating the endoscope clockwise when the distal part is located near the viewing point in a case where the direction of rotation of the looped portion is clockwise;
   rotating the endoscope counterclockwise when the distal part is located away from the viewing point in the case where the direction of rotation of the looped portion is clockwise; and
   rotating the endoscope counterclockwise when the distal part is located near the viewing point in the case where the direction of rotation of the looped portion is counterclockwise.

21. An endoscopic information processing method, comprising:
   a shape analyzing step of analyzing an insertional shape acquired by detecting the shape of an insertion unit of an endoscope that is inserted into a body cavity, the shape analyzing step including:
   detecting a looped portion along the insertion unit,
   calculating a direction of rotation and a size of a looped portion where a loop is formed by an insertion operation of the insertion unit,
   calculating a direction of a plane on which the detected looped portion is formed, and
   determining whether a distal part of the insertion unit is located closer to or farther from a viewing point relative to the plane on which the looped portion is formed, the viewing point being a position or angle from which the representation of the endoscope is being viewed on a display; and
   an information providing step of providing an operating method for bringing the insertion unit from a current situation into a situation in which a loop is canceled based on results of analysis performed at the shape analyzing step, the operating method being a series of steps for manipulating the endoscope to be carried out in succession provided in graphical, written, and/or audio form,
   the information providing step, using the analysis performed at the shape analyzing step determining the operating method in order to cancel a looped state of the insertion unit by straightening the insertion unit.

22. An endoscopic information processing method according to claim 21, further comprising a shape storing step of storing a plurality of insertional shapes acquired by detecting the shape of an insertion unit of an endoscope that is inserted into a body cavity, wherein:
   at the shape analyzing step, the shape of the endoscope insertion unit is analyzed based on the plurality of shapes of the endoscope insertion unit stored at the shape storing step.

23. An endoscopic information processing method according to claim 21, wherein at the information providing step, information on the shape of the endoscope insertion unit is provided based on the analysis performed at the shape analyzing step.

24. An endoscopic information processing method according to claim 21, further comprising:
- a first data preserving step of preserving first data that is the operating method provided at the information providing step;
- a second data preserving step of preserving second data, which is examination information containing an endoscopic image and received from an endoscope system, in association with the first data; and
- a reproducing step of presenting, through a monitor, the first and second data preserved in the preserving steps, synchronously with each other or independently of each other.

25. The endoscopic information processing method according to claim 21, wherein at the information providing step, one method determined among straightening operation methods is provided in graphical, written, and/or audio form, the straightening operation methods including:
- rotating the endoscope clockwise when the distal part is located away from the viewing point in a case where the direction of rotation of the looped portion is counterclockwise;
- rotating the endoscope clockwise when the distal part is located near the viewing point in a case where the direction of rotation of the looped portion is clockwise;
- rotating the endoscope counterclockwise when the distal part is located away from the viewing point in the case where the direction of rotation of the looped portion is clockwise; and
- rotating the endoscope counterclockwise when the distal part is located near the viewing point in the case where the direction of rotation of the looped portion is counterclockwise.

* * * * *